United States Patent
Conway et al.

(10) Patent No.: US 10,092,728 B2
(45) Date of Patent: Oct. 9, 2018

(54) SHEATH FOR SECURING URINARY CATHETER

(71) Applicant: Rochester Medical, Stewartville, MN (US)

(72) Inventors: Anthony J. Conway, Chatfield, MN (US); Sarah L. Grinde, Spring Grove, MN (US)

(73) Assignee: Rochester Medical Corporation, a subsidiary of C.R. Bard, Inc., Stewartville, MN (US)

( * ) Notice: Subject to any disclaimer, the term of this patent is extended or adjusted under 35 U.S.C. 154(b) by 1030 days.

(21) Appl. No.: 13/682,406

(22) Filed: Nov. 20, 2012

(65) Prior Publication Data
US 2014/0142554 A1 May 22, 2014

(51) Int. Cl.
*A61M 25/02* (2006.01)

(52) U.S. Cl.
CPC ..... *A61M 25/02* (2013.01); *A61M 2025/0213* (2013.01); *A61M 2210/167* (2013.01)

(58) Field of Classification Search
CPC .. A61F 5/451; A61F 5/453; A61F 6/02; A61F 6/04; A61F 2006/02; A61F 2006/04; A61F 2005/445; A61M 25/0017; A61M 25/002; A61M 25/0021; A61M 25/0043; A61M 25/0067; A61M 25/0068; A61M 25/0074; A61M 25/01–25/02
USPC ........................................ 604/352, 180, 544
See application file for complete search history.

(56) References Cited

U.S. PATENT DOCUMENTS

| | | | |
|---|---|---|---|
| 480,911 | A | 8/1892 | Vance |
| 822,092 | A | 5/1906 | Woodruff |
| 1,235,142 | A | 7/1917 | Ichilian |
| 1,643,289 | A | 9/1927 | Peglay |
| 1,661,494 | A | 3/1928 | Nielsen |
| 2,043,630 | A | 6/1936 | Raiche |
| 2,213,210 | A | 9/1940 | Egbert |
| 2,228,992 | A | 1/1941 | Fry |
| 2,230,226 | A | 2/1941 | Auzin |
| 2,248,934 | A | 7/1941 | Auzin |
| 2,285,502 | A | 6/1942 | Dreyfus |

(Continued)

FOREIGN PATENT DOCUMENTS

| | | |
|---|---|---|
| CA | 763930 A | 7/1967 |
| CN | 2139835 Y | 8/1993 |

(Continued)

OTHER PUBLICATIONS

Amirkhalili, Saeid et al., "Mitric Oxide Complexes of Trimethylaluminium," Jornal of Organometallic Chemistry, 149 (Jan. 20, 1978) 407-411.

(Continued)

*Primary Examiner* — Tatyana Zalukaeva
*Assistant Examiner* — Kai Weng
(74) *Attorney, Agent, or Firm* — Rutan & Tucker, LLP

(57) ABSTRACT

The present invention relates to a device that secures a straight or Foley catheter in the urinary tract of a male subject. The device includes a portion that can be coupled to the subject's penis and a portion that can be coupled to the straight or Foley catheter. The present invention also relates to methods of making and using this device and to assemblies including the device and a straight or Foley catheter.

21 Claims, 6 Drawing Sheets

(56) References Cited

U.S. PATENT DOCUMENTS

| | | |
|---|---|---|
| 2,308,484 A | 1/1943 | Auzin et al. |
| 2,314,262 A | 3/1943 | Winder |
| 2,320,157 A | 5/1943 | Raiche |
| 2,322,858 A | 6/1943 | Limbert et al. |
| 2,330,399 A | 9/1943 | Winder |
| 2,330,400 A | 9/1943 | Winder |
| 2,389,831 A | 11/1945 | Welsh |
| 2,390,070 A | 12/1945 | Auzin |
| 2,481,488 A | 9/1949 | Auzin |
| 2,494,393 A | 1/1950 | Lamson |
| 2,610,626 A | 9/1952 | Edwards |
| 2,638,093 A | 5/1953 | Kulick |
| 2,649,619 A | 8/1953 | Killian |
| 2,649,854 A | 8/1953 | Salm |
| 2,690,595 A | 10/1954 | Raiche |
| 2,712,161 A | 7/1955 | Moss |
| 2,856,932 A | 10/1958 | Griffitts |
| 2,912,981 A | 11/1959 | Keough |
| 3,044,468 A | 7/1962 | Birtwell |
| 3,053,257 A | 9/1962 | Birtwell |
| 3,076,464 A | 2/1963 | Rosenberg |
| 3,154,080 A | 10/1964 | Rowan et al. |
| 3,169,527 A | 2/1965 | Sheridan |
| 3,211,151 A | 10/1965 | Foderick et al. |
| 3,304,353 A | 2/1967 | Harautuneian |
| 3,345,988 A | 10/1967 | Vitello |
| 3,394,704 A | 7/1968 | Dery |
| 3,394,705 A | 7/1968 | Abramson |
| 3,403,682 A | 10/1968 | McDonell |
| 3,409,016 A | 11/1968 | Foley |
| 3,434,869 A | 3/1969 | Davidson |
| 3,463,141 A | 8/1969 | Mozolf |
| 3,503,400 A | 3/1970 | Osthagen |
| 3,508,959 A | 4/1970 | Krahnke |
| 3,509,884 A | 5/1970 | Bell |
| 3,520,305 A | 7/1970 | Davis |
| 3,539,674 A | 11/1970 | Dereniuk et al. |
| 3,544,668 A | 12/1970 | Dereniuk |
| 3,548,805 A | 12/1970 | Datsenko |
| 3,556,294 A | 1/1971 | Walck et al. |
| 3,566,874 A | 3/1971 | Shepherd et al. |
| 3,593,713 A | 7/1971 | Bogoff et al. |
| 3,598,127 A | 8/1971 | Wepsic |
| 3,606,889 A | 9/1971 | Arblaster |
| 3,642,004 A | 2/1972 | Osthagen et al. |
| 3,646,929 A | 3/1972 | Bonnar |
| 3,648,704 A | 3/1972 | Jackson |
| 3,683,928 A | 8/1972 | Kuntz |
| 3,695,921 A | 10/1972 | Shepard et al. |
| 3,699,956 A | 10/1972 | Kitrilakis et al. |
| 3,699,964 A | 10/1972 | Ericson |
| 3,708,324 A | 1/1973 | Stebleton |
| 3,726,281 A | 4/1973 | Norton et al. |
| 3,739,783 A | 6/1973 | Broerman |
| 3,762,399 A | 10/1973 | Riedell |
| 3,768,102 A | 10/1973 | Kwan-Gett et al. |
| 3,788,324 A | 1/1974 | Lim |
| 3,794,042 A | 2/1974 | De Klotz et al. |
| 3,797,478 A | 3/1974 | Walsh et al. |
| 3,838,728 A | 10/1974 | Voegele |
| 3,841,304 A | 10/1974 | Jones |
| 3,854,483 A | 12/1974 | Powers |
| 3,861,395 A | 1/1975 | Taniguchi |
| 3,875,937 A | 4/1975 | Schmitt et al. |
| 3,879,516 A | 4/1975 | Wolvek |
| 3,882,220 A | 5/1975 | Ryder |
| 3,889,685 A | 6/1975 | Miller, Jr. et al. |
| 3,894,540 A | 7/1975 | Bonner, Jr. |
| 3,898,993 A | 8/1975 | Taniguchi |
| 3,903,893 A | 9/1975 | Scheer |
| 3,924,634 A | 12/1975 | Taylor et al. |
| 3,926,705 A | 12/1975 | Todd |
| 3,930,580 A | 1/1976 | Bazell et al. |
| 3,934,721 A | 1/1976 | Juster et al. |
| 3,962,519 A | 6/1976 | Rusch et al. |
| 3,967,728 A | 7/1976 | Gordon et al. |
| 3,981,299 A | 9/1976 | Murray |
| 3,983,879 A | 10/1976 | Todd |
| 4,026,296 A | 5/1977 | Stoy et al. |
| 4,029,104 A | 6/1977 | Kerber |
| 4,055,682 A | 10/1977 | Merrill |
| 4,062,363 A | 12/1977 | Bonner, Jr. |
| 4,091,922 A | 5/1978 | Egler |
| 4,119,094 A | 10/1978 | Micklus et al. |
| 4,120,715 A | 10/1978 | Ockwell et al. |
| 4,133,303 A | 1/1979 | Patel |
| 4,140,127 A | 2/1979 | Cianci et al. |
| 4,149,539 A | 4/1979 | Cianci |
| 4,168,699 A | 9/1979 | Hauser |
| 4,186,745 A | 2/1980 | Lewis et al. |
| 4,187,851 A | 2/1980 | Hauser |
| 4,196,731 A | 4/1980 | Laurin et al. |
| 4,198,983 A | 4/1980 | Becker et al. |
| 4,198,984 A | 4/1980 | Taylor |
| 4,209,010 A | 6/1980 | Ward et al. |
| 4,225,371 A | 9/1980 | Taylor et al. |
| 4,230,115 A | 10/1980 | Walz, Jr. et al. |
| 4,246,909 A | 1/1981 | Wu et al. |
| 4,249,535 A | 2/1981 | Hargest, III |
| 4,252,760 A | 2/1981 | Foster et al. |
| 4,265,848 A | 5/1981 | Rusch et al. |
| 4,266,999 A | 5/1981 | Baier |
| 4,269,310 A | 5/1981 | Uson et al. |
| 4,284,459 A | 8/1981 | Patel et al. |
| 4,287,227 A | 9/1981 | Kamada et al. |
| 4,311,146 A | 1/1982 | Wonder |
| 4,311,659 A | 1/1982 | Rey et al. |
| 4,318,406 A | 3/1982 | McLeod |
| 4,318,947 A | 3/1982 | Joung |
| 4,341,817 A | 7/1982 | Tozier et al. |
| 4,342,392 A | 8/1982 | Cox |
| 4,343,788 A | 8/1982 | Mustacich et al. |
| 4,366,901 A | 1/1983 | Short |
| 4,367,732 A | 1/1983 | Poulsen et al. |
| 4,378,018 A | 3/1983 | Alexander et al. |
| 4,378,796 A | 4/1983 | Milhaud |
| 4,379,506 A | 4/1983 | Davidson |
| 4,381,008 A | 4/1983 | Thomas et al. |
| 4,381,380 A | 4/1983 | LeVeen et al. |
| 4,395,806 A | 8/1983 | Wonder et al. |
| 4,411,648 A | 10/1983 | Davis et al. |
| 4,419,097 A * | 12/1983 | Rowland ................ 604/174 |
| 4,428,365 A | 1/1984 | Hakky |
| 4,446,860 A | 5/1984 | Gutnick |
| 4,457,299 A | 7/1984 | Cornwell |
| 4,472,226 A | 9/1984 | Redinger et al. |
| 4,475,910 A | 10/1984 | Conway et al. |
| 4,477,325 A | 10/1984 | Osburn |
| 4,479,795 A | 10/1984 | Mustacich et al. |
| 4,515,593 A | 5/1985 | Norton |
| 4,534,768 A | 8/1985 | Osburn et al. |
| 4,539,234 A | 9/1985 | Sakamoto et al. |
| 4,540,409 A | 9/1985 | Nystrom et al. |
| 4,553,533 A | 11/1985 | Leighton |
| 4,563,184 A | 1/1986 | Korol |
| 4,568,340 A | 2/1986 | Giacalone |
| 4,571,239 A | 2/1986 | Heyman |
| 4,571,240 A | 2/1986 | Samson et al. |
| 4,576,599 A | 3/1986 | Lipner |
| 4,581,026 A | 4/1986 | Schneider |
| 4,581,028 A | 4/1986 | Fox, Jr. et al. |
| 4,582,762 A | 4/1986 | Onohara et al. |
| 4,586,974 A | 5/1986 | Nystrom et al. |
| 4,589,874 A | 5/1986 | Riedel et al. |
| 4,592,920 A | 6/1986 | Murtfeldt |
| 4,597,765 A | 7/1986 | Klatt |
| 4,597,931 A | 7/1986 | Watanabe et al. |
| 4,601,713 A | 7/1986 | Fuqua |
| 4,603,152 A | 7/1986 | Laurin et al. |
| 4,612,337 A | 9/1986 | Fox, Jr. et al. |
| 4,613,324 A | 9/1986 | Ghajar |
| 4,615,692 A | 10/1986 | Giacalone et al. |
| 4,615,697 A | 10/1986 | Robinson |
| 4,622,033 A | 11/1986 | Taniguchi |

(56) References Cited

U.S. PATENT DOCUMENTS

| | | |
|---|---|---|
| 4,623,329 A | 11/1986 | Drobish et al. |
| 4,626,250 A | 12/1986 | Schneider |
| 4,627,844 A | 12/1986 | Schmitt |
| 4,633,863 A * | 1/1987 | Filips et al. ............... 128/846 |
| 4,634,433 A | 1/1987 | Osborne |
| 4,637,907 A | 1/1987 | Hegel et al. |
| 4,638,790 A | 1/1987 | Conway et al. |
| 4,640,668 A | 2/1987 | Yang |
| 4,640,688 A | 2/1987 | Hauser |
| 4,652,259 A | 3/1987 | O'Neil |
| 4,664,657 A | 5/1987 | Williamitis et al. |
| 4,673,401 A | 6/1987 | Jensen et al. |
| 4,677,143 A | 6/1987 | Laurin et al. |
| 4,685,913 A | 8/1987 | Austin |
| 4,686,124 A | 8/1987 | Onohara et al. |
| 4,687,470 A | 8/1987 | Okada |
| 4,692,152 A | 9/1987 | Emde |
| 4,699,616 A | 10/1987 | Nowak et al. |
| 4,710,169 A | 12/1987 | Christopher |
| 4,710,181 A | 12/1987 | Fuqua |
| 4,731,064 A | 3/1988 | Heyden |
| 4,737,219 A | 4/1988 | Taller et al. |
| 4,739,768 A | 4/1988 | Engelson |
| 4,747,845 A | 5/1988 | Korol |
| 4,754,877 A | 7/1988 | Johansson et al. |
| 4,759,753 A | 7/1988 | Schneider et al. |
| 4,768,503 A * | 9/1988 | Highgate et al. ............... 602/52 |
| 4,769,013 A | 9/1988 | Lorenz et al. |
| 4,769,099 A | 9/1988 | Therriault et al. |
| 4,772,473 A | 9/1988 | Patel et al. |
| 4,773,901 A | 9/1988 | Norton |
| 4,775,371 A | 10/1988 | Mueller, Jr. |
| 4,790,834 A | 12/1988 | Austin |
| 4,790,835 A | 12/1988 | Elias |
| D299,865 S | 2/1989 | Kamstrup-Larsen et al. |
| 4,810,247 A | 3/1989 | Glassman |
| 4,811,847 A | 3/1989 | Reif et al. |
| 4,813,935 A | 3/1989 | Haber et al. |
| 4,820,270 A | 4/1989 | Hardcastle et al. |
| 4,820,289 A | 4/1989 | Coury et al. |
| 4,820,291 A | 4/1989 | Terauchi et al. |
| 4,820,292 A | 4/1989 | Korol et al. |
| 4,834,721 A | 5/1989 | Onohara et al. |
| 4,838,876 A | 6/1989 | Wong et al. |
| 4,846,784 A | 7/1989 | Haber |
| 4,846,909 A | 7/1989 | Klug et al. |
| 4,850,969 A | 7/1989 | Jackson |
| 4,861,337 A | 8/1989 | George |
| 4,863,424 A | 9/1989 | Blake, III et al. |
| 4,863,444 A | 9/1989 | Blomer |
| 4,863,449 A | 9/1989 | Therriault et al. |
| 4,867,748 A | 9/1989 | Samuelsen |
| 4,874,373 A | 10/1989 | Luther et al. |
| 4,876,109 A | 10/1989 | Mayer et al. |
| 4,885,049 A | 12/1989 | Johannesson |
| 4,894,059 A | 1/1990 | Larsen et al. |
| 4,902,503 A | 2/1990 | Umemura et al. |
| 4,904,260 A | 2/1990 | Ray et al. |
| 4,917,113 A | 4/1990 | Conway et al. |
| 4,917,686 A | 4/1990 | Bayston et al. |
| 4,919,966 A | 4/1990 | Shlenker |
| RE33,206 E | 5/1990 | Conway et al. |
| 4,923,450 A | 5/1990 | Maeda et al. |
| 4,925,668 A | 5/1990 | Khan et al. |
| 4,930,522 A | 6/1990 | Busnel et al. |
| 4,931,056 A | 6/1990 | Ghajar et al. |
| 4,932,938 A | 6/1990 | Goldberg et al. |
| 4,932,948 A | 6/1990 | Kernes et al. |
| 4,934,999 A | 6/1990 | Bader |
| 4,935,260 A | 6/1990 | Shlenker |
| 4,950,256 A | 8/1990 | Luther et al. |
| 4,952,618 A | 8/1990 | Olsen |
| 4,963,137 A | 10/1990 | Heyden |
| 4,968,294 A | 11/1990 | Salama |
| 4,968,507 A | 11/1990 | Zentner et al. |
| 4,976,703 A | 12/1990 | Franetzki et al. |
| 4,981,471 A | 1/1991 | Quinn et al. |
| 4,994,047 A | 2/1991 | Walker et al. |
| 5,004,454 A | 4/1991 | Beyar et al. |
| 5,007,897 A | 4/1991 | Kalb et al. |
| 5,013,306 A | 5/1991 | Solomon et al. |
| 5,013,717 A | 5/1991 | Solomon et al. |
| 5,019,096 A | 5/1991 | Fox, Jr. et al. |
| 5,019,378 A | 5/1991 | Allen |
| 5,019,601 A | 5/1991 | Allen |
| 5,059,190 A | 10/1991 | Novak |
| 5,071,406 A | 12/1991 | Jang |
| 5,078,707 A | 1/1992 | Klug |
| 5,082,006 A | 1/1992 | Jonasson |
| 5,084,037 A | 1/1992 | Barnett |
| 5,087,252 A | 2/1992 | Denard |
| 5,088,980 A | 2/1992 | Leighton |
| 5,089,205 A | 2/1992 | Huang et al. |
| 5,090,424 A | 2/1992 | Simon et al. |
| 5,098,379 A | 3/1992 | Conway et al. |
| 5,102,401 A | 4/1992 | Lambert et al. |
| 5,102,405 A | 4/1992 | Conway et al. |
| 5,109,378 A | 4/1992 | Proctor et al. |
| 5,109,601 A | 5/1992 | McBride |
| 5,112,306 A | 5/1992 | Burton et al. |
| 5,114,398 A | 5/1992 | Trick et al. |
| 5,128,088 A | 7/1992 | Shimomura et al. |
| 5,131,906 A | 7/1992 | Chen |
| 5,137,671 A | 8/1992 | Conway et al. |
| 5,140,999 A | 8/1992 | Ardito |
| 5,147,341 A | 9/1992 | Starke et al. |
| 5,165,952 A | 11/1992 | Solomon et al. |
| 5,176,666 A | 1/1993 | Conway et al. |
| 5,197,957 A | 3/1993 | Wendler |
| 5,201,724 A | 4/1993 | Hukins et al. |
| 5,209,726 A | 5/1993 | Goosen |
| 5,211,640 A | 5/1993 | Wendler |
| 5,226,530 A | 7/1993 | Golden |
| 5,234,411 A | 8/1993 | Vaillancourt |
| 5,236,422 A | 8/1993 | Eplett, Jr. |
| 5,242,391 A | 9/1993 | Place et al. |
| 5,242,428 A | 9/1993 | Palestrant |
| 5,261,896 A | 11/1993 | Conway et al. |
| 5,263,947 A | 11/1993 | Kay |
| 5,269,755 A | 12/1993 | Bodicky |
| 5,269,770 A | 12/1993 | Conway et al. |
| 5,270,358 A | 12/1993 | Asmus |
| 5,279,600 A | 1/1994 | Hogan |
| 5,290,306 A | 3/1994 | Trotta et al. |
| 5,300,052 A | 4/1994 | Kubo |
| 5,306,226 A | 4/1994 | Salama |
| 5,334,175 A | 8/1994 | Conway et al. |
| 5,335,775 A | 8/1994 | Scanlon et al. |
| 5,336,211 A | 8/1994 | Metz |
| 5,346,483 A | 9/1994 | Thaxton, Sr. |
| 5,348,536 A | 9/1994 | Young et al. |
| 5,352,182 A | 10/1994 | Kalb et al. |
| 5,360,402 A | 11/1994 | Conway et al. |
| 5,366,449 A | 11/1994 | Gilberg |
| 5,368,575 A | 11/1994 | Chang |
| 5,370,899 A | 12/1994 | Conway et al. |
| 5,376,085 A | 12/1994 | Conway et al. |
| 5,380,312 A | 1/1995 | Goulter |
| 5,395,333 A | 3/1995 | Brill |
| 5,402,886 A | 4/1995 | McGlinch |
| 5,409,495 A | 4/1995 | Osborn |
| 5,415,635 A | 5/1995 | Bagaoisan et al. |
| 5,417,226 A | 5/1995 | Juma |
| 5,417,666 A | 5/1995 | Coulter |
| 5,423,784 A | 6/1995 | Metz |
| 5,433,705 A | 7/1995 | Giebel et al. |
| 5,433,713 A | 7/1995 | Trotta |
| 5,447,231 A | 9/1995 | Kastenhofer |
| 5,451,424 A | 9/1995 | Solomon et al. |
| 5,454,798 A | 10/1995 | Kubalak et al. |
| 5,464,650 A | 11/1995 | Berg et al. |
| 5,479,945 A | 1/1996 | Simon |
| 5,482,740 A | 1/1996 | Conway et al. |
| 5,483,976 A | 1/1996 | McLaughlin et al. |

(56) References Cited

U.S. PATENT DOCUMENTS

| | | |
|---|---|---|
| 5,501,669 A | 3/1996 | Conway et al. |
| 5,509,427 A | 4/1996 | Simon et al. |
| 5,513,659 A | 5/1996 | Buuck et al. |
| 5,513,660 A | 5/1996 | Simon et al. |
| 5,531,715 A | 7/1996 | Engelson et al. |
| 5,531,717 A | 7/1996 | Roberto et al. |
| 5,538,584 A | 7/1996 | Metz |
| 5,549,924 A | 8/1996 | Shlenker et al. |
| 5,554,141 A | 9/1996 | Wendler |
| 5,562,599 A | 10/1996 | Beyschlag |
| 5,567,495 A | 10/1996 | Modak et al. |
| 5,569,219 A | 10/1996 | Hakki et al. |
| 5,582,599 A | 12/1996 | Daneshvar |
| 5,593,718 A | 1/1997 | Conway et al. |
| 5,599,321 A | 2/1997 | Conway et al. |
| 5,614,143 A | 3/1997 | Hager |
| 5,622,711 A | 4/1997 | Chen |
| 5,624,395 A | 4/1997 | Mikhail et al. |
| 5,630,429 A | 5/1997 | Dann |
| 5,633,010 A | 5/1997 | Chen |
| 5,643,235 A | 7/1997 | Figuerido |
| 5,670,111 A | 9/1997 | Conway et al. |
| 5,670,557 A | 9/1997 | Dietz et al. |
| 5,671,755 A | 9/1997 | Simon et al. |
| 5,674,561 A | 10/1997 | Dietz et al. |
| 5,679,399 A | 10/1997 | Shlenker et al. |
| 5,695,485 A | 12/1997 | Duperret et al. |
| 5,702,381 A | 12/1997 | Cottenden |
| 5,707,357 A | 1/1998 | Mikhail et al. |
| 5,709,672 A | 1/1998 | Illner |
| 5,711,841 A | 1/1998 | Jaker |
| 5,724,994 A | 3/1998 | Simon et al. |
| 5,730,733 A | 3/1998 | Mortier et al. |
| 5,736,152 A | 4/1998 | Dunn |
| 5,752,525 A | 5/1998 | Simon et al. |
| 5,756,144 A | 5/1998 | Wolff et al. |
| 5,762,996 A | 6/1998 | Lucas et al. |
| 5,779,632 A | 7/1998 | Dietz et al. |
| 5,779,670 A | 7/1998 | Bidwell et al. |
| 5,795,332 A | 8/1998 | Lucas et al. |
| 5,795,334 A | 8/1998 | Cochrane, III |
| 5,795,524 A | 8/1998 | Basso, Jr. et al. |
| 5,806,527 A | 9/1998 | Borodulin et al. |
| 5,810,789 A | 9/1998 | Powers et al. |
| 5,820,607 A | 10/1998 | Tcholakian et al. |
| 5,827,247 A | 10/1998 | Kay |
| 5,827,249 A | 10/1998 | Jensen |
| 5,830,932 A | 11/1998 | Kay |
| 5,853,518 A | 12/1998 | Utas et al. |
| 5,853,750 A | 12/1998 | Dietz et al. |
| 5,877,243 A | 3/1999 | Sarangapani |
| 5,895,374 A | 4/1999 | Rodsten et al. |
| 5,897,535 A | 4/1999 | Feliziani et al. |
| 5,902,631 A | 5/1999 | Wang et al. |
| 5,906,575 A | 5/1999 | Conway et al. |
| 5,931,303 A | 8/1999 | Salvadori |
| 5,931,304 A | 8/1999 | Hammond |
| 5,971,954 A | 10/1999 | Conway et al. |
| 5,980,483 A | 11/1999 | Dimitri et al. |
| 5,980,507 A | 11/1999 | Fassuliotis et al. |
| 6,004,305 A | 12/1999 | Hursman et al. |
| 6,007,524 A | 12/1999 | Schneider |
| 6,007,526 A | 12/1999 | Passalaqua et al. |
| 6,050,934 A | 4/2000 | Mikhail et al. |
| 6,053,905 A | 4/2000 | Daignault, Jr. et al. |
| 6,059,107 A | 5/2000 | Nosted et al. |
| 6,063,063 A | 5/2000 | Harboe et al. |
| 6,065,597 A | 5/2000 | Pettersson et al. |
| 6,090,075 A | 7/2000 | House |
| 6,098,625 A | 8/2000 | Winkler |
| 6,102,929 A | 8/2000 | Conway et al. |
| 6,113,582 A | 9/2000 | Dwork |
| 6,119,697 A | 9/2000 | Engel et al. |
| 6,131,575 A | 10/2000 | Lenker et al. |
| 6,132,399 A | 10/2000 | Shultz |
| 6,186,990 B1 | 2/2001 | Chen et al. |
| 6,206,885 B1 | 3/2001 | Ghahremani et al. |
| 6,231,501 B1 | 5/2001 | Ditter |
| 6,254,570 B1 | 7/2001 | Rutner et al. |
| 6,261,255 B1 | 7/2001 | Mullis et al. |
| 6,261,271 B1 | 7/2001 | Solomon et al. |
| 6,280,425 B1 | 8/2001 | Del Guercio |
| 6,296,627 B1 | 10/2001 | Edwards |
| 6,299,598 B1 | 10/2001 | Bander |
| 6,315,711 B1 | 11/2001 | Conway et al. |
| 6,326,421 B1 | 12/2001 | Lipman |
| 6,355,004 B1 | 3/2002 | Pedersen et al. |
| 6,379,334 B1 | 4/2002 | Frassica |
| 6,383,434 B2 | 5/2002 | Conway et al. |
| 6,387,080 B1 | 5/2002 | Rodsten |
| 6,391,010 B1 | 5/2002 | Wilcox |
| 6,402,726 B1 | 6/2002 | Genese |
| 6,409,717 B1 | 6/2002 | Israelsson et al. |
| 6,437,038 B1 | 8/2002 | Chen |
| 6,440,060 B1 | 8/2002 | Latour, Jr. |
| 6,468,245 B2 | 10/2002 | Alexandersen et al. |
| 6,479,000 B2 | 11/2002 | Conway et al. |
| 6,479,726 B1 | 11/2002 | Cole |
| 6,509,319 B1 | 1/2003 | Raad et al. |
| 6,551,293 B1 | 4/2003 | Mitchell |
| 6,558,369 B2 | 5/2003 | Rosenblum |
| 6,558,792 B1 | 5/2003 | Vaabengaard et al. |
| 6,578,709 B1 | 6/2003 | Kavanagh et al. |
| 6,579,539 B2 | 6/2003 | Lawson et al. |
| 6,582,401 B1 | 6/2003 | Windheuser et al. |
| 6,596,401 B1 | 7/2003 | Terry et al. |
| 6,602,244 B2 | 8/2003 | Kavanagh et al. |
| 6,613,014 B1 | 9/2003 | Chi |
| 6,626,888 B1 | 9/2003 | Conway et al. |
| 6,632,204 B2 | 10/2003 | Guldfeldt et al. |
| 6,634,498 B2 | 10/2003 | Kayerod et al. |
| 6,638,269 B2 | 10/2003 | Wilcox |
| 6,659,937 B2 | 12/2003 | Polsky et al. |
| 6,682,555 B2 | 1/2004 | Cioanta et al. |
| 6,693,189 B2 | 2/2004 | Holt et al. |
| 6,695,831 B1 | 2/2004 | Tsukada et al. |
| 6,716,895 B1 | 4/2004 | Terry |
| 6,719,709 B2 | 4/2004 | Whalen et al. |
| 6,723,350 B2 | 4/2004 | Burrell et al. |
| 6,733,474 B2 | 5/2004 | Kusleika |
| 6,736,805 B2 | 5/2004 | Israelsson et al. |
| 6,740,273 B2 | 5/2004 | Lee |
| 6,767,551 B2 | 7/2004 | McGhee et al. |
| D496,266 S | 9/2004 | Nestenborg et al. |
| 6,787,156 B1 | 9/2004 | Bar-Shalom |
| 6,797,743 B2 | 9/2004 | McDonald et al. |
| 6,803,420 B2 | 10/2004 | Cleary et al. |
| 6,848,574 B1 | 2/2005 | Israelsson et al. |
| 6,849,070 B1 | 2/2005 | Hansen et al. |
| 6,852,105 B2 | 2/2005 | Bolmsjo et al. |
| D503,335 S | 3/2005 | Risberg et al. |
| 6,869,416 B2 | 3/2005 | Windheuser et al. |
| 6,872,195 B2 | 3/2005 | Modak et al. |
| 6,887,230 B2 | 5/2005 | Kubalak et al. |
| 6,939,339 B1 | 9/2005 | Axexandersen et al. |
| 6,939,554 B2 | 9/2005 | McDonald et al. |
| 6,949,090 B1 | 9/2005 | Leers et al. |
| 6,951,902 B2 | 10/2005 | McDonald et al. |
| 7,001,370 B2 | 2/2006 | Kubalak et al. |
| 7,033,367 B2 | 4/2006 | Ghahremani et al. |
| 7,066,912 B2 | 6/2006 | Nestenborg et al. |
| 7,087,048 B2 | 8/2006 | Israelsson et al. |
| 7,094,220 B2 | 8/2006 | Tanghoj et al. |
| 7,160,277 B2 | 1/2007 | Elson et al. |
| 7,166,092 B2 | 1/2007 | Elson et al. |
| 7,204,940 B2 | 4/2007 | McDonald et al. |
| 7,211,275 B2 | 5/2007 | Ying et al. |
| 7,294,117 B2 | 11/2007 | Provost-tine et al. |
| 7,311,698 B2 | 12/2007 | Tanghoj et al. |
| 7,329,412 B2 | 2/2008 | Modak et al. |
| 7,331,948 B2 | 2/2008 | Skarda |
| 7,334,679 B2 | 2/2008 | Givens, Jr. |
| 7,374,040 B2 | 5/2008 | Lee et al. |
| 7,380,658 B2 | 6/2008 | Murray et al. |

(56) References Cited

U.S. PATENT DOCUMENTS

| | | |
|---|---|---|
| 7,381,768 B2 | 6/2008 | Wiercinski et al. |
| 7,402,559 B2 | 7/2008 | Catania et al. |
| 7,445,812 B2 | 11/2008 | Schmidt et al. |
| 7,458,964 B2 | 12/2008 | Mosler et al. |
| 7,476,223 B2 | 1/2009 | McBride |
| 7,507,229 B2 | 3/2009 | Hewitt et al. |
| 7,517,343 B2 | 4/2009 | Tanghoj et al. |
| 7,571,804 B2 | 8/2009 | Kjellmann Bruun et al. |
| 7,601,158 B2 | 10/2009 | House |
| 7,615,045 B2 | 11/2009 | Israelsson et al. |
| 7,628,784 B2 | 12/2009 | Diaz et al. |
| 7,632,256 B2 | 12/2009 | Mosler et al. |
| D609,819 S | 2/2010 | Tomes et al. |
| 7,662,146 B2 | 2/2010 | House |
| 7,670,331 B2 | 3/2010 | Tanghoej |
| 7,682,353 B2 | 3/2010 | Tanghoj et al. |
| 7,691,476 B2 | 4/2010 | Finley |
| 7,717,902 B2 | 5/2010 | Sauer |
| 7,749,529 B2 | 7/2010 | Ash et al. |
| 7,767,291 B2 | 8/2010 | Taylor |
| 7,770,726 B2 | 8/2010 | Murray et al. |
| 7,770,728 B2 | 8/2010 | Kaern |
| 7,780,642 B2 | 8/2010 | Rasmussen et al. |
| 7,789,873 B2 | 9/2010 | Kubalak et al. |
| 7,823,722 B2 | 11/2010 | Bezou et al. |
| 7,846,133 B2 | 12/2010 | Windheuser et al. |
| 7,867,220 B2 | 1/2011 | Tanghoj |
| 7,886,907 B2 | 2/2011 | Murray et al. |
| 7,918,831 B2 | 4/2011 | House |
| 7,938,838 B2 | 5/2011 | House |
| 7,947,021 B2 | 5/2011 | Bourne et al. |
| 7,985,217 B2 | 7/2011 | Mosler et al. |
| 8,011,505 B2 | 9/2011 | Murray et al. |
| 8,051,981 B2 | 11/2011 | Murray et al. |
| 8,052,673 B2 | 11/2011 | Nestenborg |
| 8,058,341 B2 | 11/2011 | Tosaki et al. |
| 8,066,693 B2 | 11/2011 | Tanghoj et al. |
| 8,127,922 B2 | 3/2012 | Nordholm et al. |
| 8,163,327 B2 | 4/2012 | Finley |
| 8,177,774 B2 | 5/2012 | House |
| 8,181,778 B1 | 5/2012 | Van Groningen et al. |
| 8,192,413 B2 | 6/2012 | Bjerregaard |
| 8,205,745 B2 | 6/2012 | Murray et al. |
| 8,207,393 B2 | 6/2012 | Bach |
| 8,230,993 B2 | 7/2012 | Tanghoej |
| 8,267,919 B2 | 9/2012 | Utas et al. |
| 8,282,624 B2 | 10/2012 | Tanghoej et al. |
| 8,287,519 B2 | 10/2012 | Smith |
| 8,298,202 B2 | 10/2012 | McCray |
| 8,303,556 B2 | 11/2012 | White |
| 8,328,792 B2 | 12/2012 | Nishtala et al. |
| 8,356,457 B2 | 1/2013 | Murray et al. |
| 8,409,171 B2 | 4/2013 | Hannon et al. |
| 8,454,569 B2 | 6/2013 | Kull-Osterlin et al. |
| 8,459,455 B2 | 6/2013 | Frojd |
| 8,475,434 B2 | 7/2013 | Frojd |
| 8,864,730 B2 | 10/2014 | Conway et al. |
| 9,707,375 B2 | 7/2017 | Conway et al. |
| 9,872,969 B2 | 1/2018 | Conway et al. |
| 2001/0001443 A1 | 5/2001 | Kayerod et al. |
| 2001/0031933 A1 | 10/2001 | Cannon |
| 2001/0054562 A1 | 12/2001 | Pettersson et al. |
| 2002/0013564 A1 | 1/2002 | Kubalek et al. |
| 2002/0032406 A1 | 3/2002 | Kusleika |
| 2002/0103467 A1 | 8/2002 | Kubalak |
| 2002/0147265 A1 | 10/2002 | Ding et al. |
| 2002/0169438 A1 | 11/2002 | Sauer |
| 2002/0182265 A1 | 12/2002 | Burrell et al. |
| 2003/0004496 A1 | 1/2003 | Tanghoj |
| 2003/0018293 A1 | 1/2003 | Tanghoj et al. |
| 2003/0018302 A1 | 1/2003 | Kavanagh et al. |
| 2003/0018321 A1 | 1/2003 | Rosenblum |
| 2003/0018322 A1 | 1/2003 | Tanghoj et al. |
| 2003/0055403 A1 | 3/2003 | Nestenborg et al. |
| 2003/0060807 A1 | 3/2003 | Tanghoj et al. |
| 2003/0083644 A1 | 5/2003 | Avaltroni |
| 2003/0114823 A1 | 6/2003 | Bosselaar et al. |
| 2003/0130646 A1 | 7/2003 | Kubalak et al. |
| 2003/0168365 A1 | 9/2003 | Kaern |
| 2004/0030301 A1 | 2/2004 | Hunter |
| 2004/0055925 A1 | 3/2004 | Franks-Farah et al. |
| 2004/0074794 A1 | 4/2004 | Conway et al. |
| 2004/0097892 A1 | 5/2004 | Evans et al. |
| 2004/0133156 A1 | 7/2004 | Diaz et al. |
| 2004/0153049 A1 | 8/2004 | Hewitt et al. |
| 2004/0153051 A1 | 8/2004 | Israelsson et al. |
| 2004/0158231 A1 | 8/2004 | Tanghoj et al. |
| 2004/0163980 A1 | 8/2004 | Tanghoj et al. |
| 2004/0193143 A1 | 9/2004 | Sauer |
| 2004/0234572 A1 | 11/2004 | Martinod et al. |
| 2004/0236293 A1 | 11/2004 | Tanghoj et al. |
| 2004/0249343 A1 | 12/2004 | Cioanta |
| 2004/0254562 A1 | 12/2004 | Tanghoj et al. |
| 2004/0256264 A1 | 12/2004 | Israelsson et al. |
| 2005/0015076 A1 | 1/2005 | Giebmeyer et al. |
| 2005/0031872 A1 | 2/2005 | Schmidt et al. |
| 2005/0043715 A1 | 2/2005 | Nestenborg et al. |
| 2005/0049577 A1 | 3/2005 | Snell et al. |
| 2005/0070882 A1 | 3/2005 | McBride |
| 2005/0080399 A1 | 4/2005 | Bolmsjo et al. |
| 2005/0096688 A1 | 5/2005 | Slazas et al. |
| 2005/0101924 A1 | 5/2005 | Elson et al. |
| 2005/0109648 A1 | 5/2005 | Kerzman et al. |
| 2005/0137582 A1 | 6/2005 | Kull-Osterlin et al. |
| 2005/0148950 A1 | 7/2005 | Windheuser et al. |
| 2005/0177104 A1 | 8/2005 | Conway |
| 2005/0199521 A1 | 9/2005 | Givens |
| 2005/0214443 A1 | 9/2005 | Madsen |
| 2005/0282977 A1 | 12/2005 | Stempel et al. |
| 2005/0283136 A1 | 12/2005 | Skarda |
| 2006/0004332 A1 | 1/2006 | Marx |
| 2006/0025753 A1 | 2/2006 | Kubalak et al. |
| 2006/0041246 A1 | 2/2006 | Provost-tine et al. |
| 2006/0058777 A1 | 3/2006 | Nielsen |
| 2006/0163097 A1 | 7/2006 | Murray et al. |
| 2006/0196783 A1 | 9/2006 | Bruun et al. |
| 2006/0229576 A1 | 10/2006 | Conway et al. |
| 2006/0240069 A1 | 10/2006 | Utas et al. |
| 2007/0016168 A1 | 1/2007 | Conway |
| 2007/0088330 A1 | 4/2007 | House |
| 2007/0149946 A1* | 6/2007 | Viswanathan et al. ....... 604/500 |
| 2007/0161971 A1 | 7/2007 | House |
| 2008/0015527 A1 | 1/2008 | House |
| 2008/0091145 A1 | 4/2008 | House |
| 2008/0103464 A1 | 5/2008 | Mosler et al. |
| 2008/0172040 A1 | 7/2008 | Smith |
| 2008/0172042 A1 | 7/2008 | House |
| 2008/0179208 A1 | 7/2008 | Murray et al. |
| 2008/0183262 A1 | 7/2008 | Dowling |
| 2008/0215021 A1* | 9/2008 | Cisko, Jr. et al. ............ 604/349 |
| 2008/0243081 A1 | 10/2008 | Nance et al. |
| 2008/0279907 A1 | 11/2008 | Ash et al. |
| 2009/0000970 A1 | 1/2009 | Bordeau et al. |
| 2009/0005725 A1 | 1/2009 | Shorey |
| 2009/0043287 A1 | 2/2009 | Mosler et al. |
| 2009/0048570 A1 | 2/2009 | Jensen |
| 2009/0101531 A1 | 4/2009 | Nordholm et al. |
| 2009/0131917 A1 | 5/2009 | Kavanagh et al. |
| 2009/0163884 A1 | 6/2009 | Kull-Osterlin et al. |
| 2009/0200187 A1 | 8/2009 | Nestenborg et al. |
| 2009/0208368 A1 | 8/2009 | Waldrep et al. |
| 2009/0221992 A1 | 9/2009 | Hannon et al. |
| 2009/0234294 A1 | 9/2009 | Harvey et al. |
| 2009/0240214 A1 | 9/2009 | Conway et al. |
| 2010/0010086 A1 | 1/2010 | Ash et al. |
| 2010/0025273 A1 | 2/2010 | Matsuda et al. |
| 2010/0030197 A1 | 2/2010 | House |
| 2010/0036363 A1 | 2/2010 | Watanabe et al. |
| 2010/0133172 A1 | 6/2010 | Song et al. |
| 2010/0155268 A1 | 6/2010 | Murray et al. |
| 2010/0200002 A1 | 8/2010 | Orban, III et al. |
| 2010/0240750 A1 | 9/2010 | Ash et al. |
| 2010/0256576 A1 | 10/2010 | Aggarwal et al. |
| 2010/0322996 A1 | 12/2010 | Wibaux et al. |

(56) References Cited

U.S. PATENT DOCUMENTS

| | | |
|---|---|---|
| 2011/0056852 A1 | 3/2011 | Frojd |
| 2011/0060317 A1 | 3/2011 | Frojd |
| 2011/0100526 A1 | 5/2011 | Umebayashi |
| 2011/0114520 A1 | 5/2011 | Matthison-Hansen |
| 2011/0118670 A1 | 5/2011 | Kay et al. |
| 2011/0137296 A1 | 6/2011 | Tanghoj |
| 2011/0152843 A1 | 6/2011 | Wedlin et al. |
| 2011/0178507 A1 | 7/2011 | Bracken et al. |
| 2011/0184386 A1 | 7/2011 | House |
| 2011/0213025 A1 | 9/2011 | Finch, Jr. |
| 2011/0284409 A1 | 11/2011 | Murray et al. |
| 2012/0029451 A1 | 2/2012 | Conway |
| 2012/0179144 A1 | 7/2012 | Carleo |
| 2012/0203182 A1 | 8/2012 | Kay et al. |
| 2012/0228165 A1 | 9/2012 | Murray et al. |
| 2012/0271101 A1 | 10/2012 | Tan |
| 2012/0316515 A1 | 12/2012 | Terry |
| 2013/0006226 A1 | 1/2013 | Hong et al. |
| 2013/0037306 A1 | 2/2013 | Kim |
| 2013/0131647 A1 | 5/2013 | Nielsen |
| 2013/0138083 A1 | 5/2013 | Tennican |
| 2013/0138088 A1 | 5/2013 | Nielsen |
| 2013/0153446 A1 | 6/2013 | Utas et al. |
| 2014/0142555 A1 | 5/2014 | Conway et al. |
| 2015/0025489 A1 | 1/2015 | Conway et al. |
| 2017/0304590 A1 | 10/2017 | Conway et al. |

FOREIGN PATENT DOCUMENTS

| | | |
|---|---|---|
| CN | 2907580 | 6/2007 |
| CN | 201248791 Y | 6/2009 |
| CN | 101896218 A | 11/2010 |
| CN | 202173496 U | 3/2012 |
| DE | 1913976 | 10/1969 |
| DE | 19826746 C1 | 11/1999 |
| EP | 0055023 A2 | 6/1982 |
| EP | 0182409 A1 | 5/1986 |
| EP | 0184629 A2 | 6/1986 |
| EP | 0187846 A1 | 7/1986 |
| EP | 0193406 A2 | 9/1986 |
| EP | 0217771 | 4/1987 |
| EP | 0218203 A1 | 4/1987 |
| EP | 0236458 A1 | 9/1987 |
| EP | 0252918 A1 | 1/1988 |
| EP | 0298634 A1 | 1/1989 |
| EP | 0303487 A2 | 2/1989 |
| EP | 0335564 A1 | 10/1989 |
| EP | 0352043 A1 | 1/1990 |
| EP | 0390720 A1 | 10/1990 |
| EP | 0407218 A1 | 1/1991 |
| EP | 0471553 A1 | 2/1992 |
| EP | 0479935 A1 | 4/1992 |
| EP | 0528965 A1 | 3/1993 |
| EP | 0553960 A1 | 8/1993 |
| EP | 0590104 A1 | 4/1994 |
| EP | 0598191 A1 | 5/1994 |
| EP | 0663196 A1 | 7/1995 |
| EP | 0677299 | 10/1995 |
| EP | 0680895 A1 | 11/1995 |
| EP | 0685179 A1 | 12/1995 |
| EP | 0699086 A1 | 3/1996 |
| EP | 0767639 A1 | 4/1997 |
| EP | 0768069 A1 | 4/1997 |
| EP | 0815037 A1 | 1/1998 |
| EP | 0909249 A1 | 4/1999 |
| EP | 0923398 | 6/1999 |
| EP | 0935478 A1 | 8/1999 |
| EP | 0959930 | 12/1999 |
| EP | 0977610 A2 | 2/2000 |
| EP | 1023882 | 8/2000 |
| EP | 1047360 A1 | 11/2000 |
| EP | 1090656 | 4/2001 |
| EP | 1115450 A1 | 7/2001 |
| EP | 1131022 A1 | 9/2001 |
| EP | 1145729 | 10/2001 |
| EP | 1245205 | 10/2002 |
| EP | 1308146 | 5/2003 |
| EP | 1347723 A1 | 10/2003 |
| EP | 1406690 A2 | 4/2004 |
| EP | 1427467 A2 | 6/2004 |
| EP | 1485158 A2 | 12/2004 |
| EP | 1498151 | 1/2005 |
| EP | 1578308 A1 | 9/2005 |
| EP | 1606196 A2 | 12/2005 |
| EP | 1615690 A1 | 1/2006 |
| EP | 1629799 A1 | 3/2006 |
| EP | 1641510 A1 | 4/2006 |
| EP | 1642610 | 4/2006 |
| EP | 1642611 | 4/2006 |
| EP | 1647298 A2 | 4/2006 |
| EP | 1786501 A2 | 5/2007 |
| EP | 1788990 A1 | 5/2007 |
| EP | 1793938 A1 | 6/2007 |
| EP | 1799163 A1 | 6/2007 |
| EP | 1904003 A2 | 4/2008 |
| EP | 1948279 A1 | 7/2008 |
| EP | 1955683 A1 | 8/2008 |
| EP | 2072075 A1 | 6/2009 |
| EP | 2216064 A1 | 8/2010 |
| EP | 2226041 A2 | 9/2010 |
| EP | 2226042 A2 | 9/2010 |
| EP | 2258435 A1 | 12/2010 |
| EP | 2275058 A1 | 1/2011 |
| EP | 2292293 A1 | 3/2011 |
| EP | 2292294 A1 | 3/2011 |
| EP | 2423125 A1 | 2/2012 |
| EP | 2423126 A1 | 2/2012 |
| EP | 2423127 A1 | 2/2012 |
| EP | 2450076 A1 | 5/2012 |
| EP | 2468347 A1 | 6/2012 |
| FR | 1558162 | 2/1969 |
| FR | 96086 | 5/1972 |
| FR | 2794638 A1 | 12/2000 |
| FR | 2855399 | 12/2004 |
| GB | 322426 A | 12/1929 |
| GB | 1131865 A | 10/1968 |
| GB | 2150938 A | 7/1985 |
| GB | 2187670 A | 9/1987 |
| WO | 1984001102 A1 | 3/1984 |
| WO | 1986000816 A1 | 2/1986 |
| WO | 1986006284 | 11/1986 |
| WO | 1987001582 A1 | 3/1987 |
| WO | 1989009626 A1 | 10/1989 |
| WO | 1990004431 A1 | 5/1990 |
| WO | 1991010466 A1 | 7/1991 |
| WO | 1991010467 A1 | 7/1991 |
| WO | 1991017728 A1 | 11/1991 |
| WO | 1992008426 A1 | 5/1992 |
| WO | 1992010220 A1 | 6/1992 |
| WO | 1992011826 A1 | 7/1992 |
| WO | 1992019192 A1 | 11/1992 |
| WO | 1993000054 A1 | 1/1993 |
| WO | 93/11821 A1 | 6/1993 |
| WO | 1993011821 A1 | 6/1993 |
| WO | 1993014806 A1 | 8/1993 |
| WO | 1994006377 A1 | 3/1994 |
| WO | 1994016747 A1 | 8/1994 |
| WO | 1994026215 A1 | 11/1994 |
| WO | 1995008968 A1 | 4/1995 |
| WO | 1995009667 A1 | 4/1995 |
| WO | 1995017862 A1 | 7/1995 |
| WO | 1995034253 A1 | 12/1995 |
| WO | 1996000541 A1 | 1/1996 |
| WO | 1996004119 A1 | 2/1996 |
| WO | 1996019254 A1 | 6/1996 |
| WO | 1996026688 A1 | 9/1996 |
| WO | 1996030277 A1 | 10/1996 |
| WO | 1996034587 A1 | 11/1996 |
| WO | 1996038192 A1 | 12/1996 |
| WO | 1996039096 A1 | 12/1996 |
| WO | 1997025947 A1 | 7/1997 |
| WO | 1997026937 | 7/1997 |
| WO | 1997041811 | 11/1997 |
| WO | 1998006642 A1 | 2/1998 |

(56) References Cited

FOREIGN PATENT DOCUMENTS

| | | |
|---|---|---|
| WO | 1999007313 A1 | 2/1999 |
| WO | 1999030761 A1 | 6/1999 |
| WO | 1999036009 A1 | 7/1999 |
| WO | 2000025848 A2 | 5/2000 |
| WO | 2000030575 A1 | 6/2000 |
| WO | 2000047494 | 8/2000 |
| WO | 2001043807 | 6/2001 |
| WO | 2001052763 | 7/2001 |
| WO | 2001093935 | 12/2001 |
| WO | 2002036192 | 5/2002 |
| WO | 2002053070 A1 | 7/2002 |
| WO | 2002060361 A2 | 8/2002 |
| WO | 03/008028 A2 | 1/2003 |
| WO | 2003002178 | 1/2003 |
| WO | 2003008029 A2 | 1/2003 |
| WO | 2003022333 A1 | 3/2003 |
| WO | 2003064279 A1 | 8/2003 |
| WO | 2003092779 | 11/2003 |
| WO | 2004004611 A1 | 1/2004 |
| WO | 2004004796 A1 | 1/2004 |
| WO | 2004030722 | 4/2004 |
| WO | 2004032992 A2 | 4/2004 |
| WO | 2004045696 | 6/2004 |
| WO | 2004050155 | 6/2004 |
| WO | 2004052440 | 6/2004 |
| WO | 2004056290 A1 | 7/2004 |
| WO | 2004056414 | 7/2004 |
| WO | 2004056909 A1 | 7/2004 |
| WO | 2004075944 | 9/2004 |
| WO | 2004089454 | 10/2004 |
| WO | 2005004964 | 1/2005 |
| WO | 2005014055 A2 | 2/2005 |
| WO | 2005061035 | 7/2005 |
| WO | 2005092418 | 10/2005 |
| WO | 2006005349 A2 | 1/2006 |
| WO | 2006009509 A1 | 1/2006 |
| WO | 2006009596 A1 | 1/2006 |
| WO | 2006017439 A2 | 2/2006 |
| WO | 2006021590 A1 | 3/2006 |
| WO | 2006027349 A1 | 3/2006 |
| WO | 2006/086250 A2 | 8/2006 |
| WO | 2006097109 A2 | 9/2006 |
| WO | 2006110695 A2 | 10/2006 |
| WO | 2006112782 A1 | 10/2006 |
| WO | 2006130776 A2 | 12/2006 |
| WO | 2007001526 A2 | 1/2007 |
| WO | 2007038988 A1 | 4/2007 |
| WO | 2007083033 A2 | 7/2007 |
| WO | 2008089770 A1 | 7/2008 |
| WO | 2008104603 A1 | 9/2008 |
| WO | 2008138351 A1 | 11/2008 |
| WO | 2008138352 A1 | 11/2008 |
| WO | 2009000277 A1 | 12/2008 |
| WO | 2009043872 A1 | 4/2009 |
| WO | 2009068043 A2 | 6/2009 |
| WO | 2009080265 A1 | 7/2009 |
| WO | 2009108243 A1 | 9/2009 |
| WO | 2010006620 A1 | 1/2010 |
| WO | 2010054659 A1 | 5/2010 |
| WO | 2010054666 A1 | 5/2010 |
| WO | 2010129362 A1 | 11/2010 |
| WO | 2010130261 A1 | 11/2010 |
| WO | 2010149174 A1 | 12/2010 |
| WO | 2010149175 A1 | 12/2010 |
| WO | 2010151682 A2 | 12/2010 |
| WO | 2011011023 A1 | 1/2011 |
| WO | 2011014201 A1 | 2/2011 |
| WO | 2011019359 A1 | 2/2011 |
| WO | 2011026929 A1 | 3/2011 |
| WO | 2011026930 A1 | 3/2011 |
| WO | 2011063816 A1 | 6/2011 |
| WO | 2011073403 A1 | 6/2011 |
| WO | 2011076211 A1 | 6/2011 |
| WO | 2011079129 A1 | 6/2011 |
| WO | 2011109393 A1 | 9/2011 |
| WO | 2012016570 A2 | 2/2012 |
| WO | 2012016571 A2 | 2/2012 |
| WO | 2012018402 A1 | 2/2012 |
| WO | 2012079590 A1 | 6/2012 |
| WO | 2012134804 A1 | 10/2012 |
| WO | 2013010745 A1 | 1/2013 |
| WO | 2013029621 A1 | 3/2013 |
| WO | 2014081853 A1 | 5/2014 |
| WO | 2014081859 A1 | 5/2014 |

OTHER PUBLICATIONS

ANGUS Chemie GmbH Technical Data Sheet for AMP-95 dated Mar. 6, 2006.
EP 12159487.3 filed Mar. 14, 2012 Exam Report dated Jul. 31, 2014.
Ethomeen C/25 Information Sheet dated Jul. 28, 2005.
Johnson, James et al., "Activities of a Nitrofurazone-Containing Urinary Catheter and a Silver Hydrogel Catheter against Multidrug-Resistant Bacteria Characteristic of Catheter-Associated Urinary Tract Infection," Antimicrobial Agents and Chemotherapy, col. 43, No. 12, Dec. 1999, pp. 2990-2995.
Lubrizol Technical Data Sheet, Neutralizing Carbopol® and Pemulen™ Polymers in Aqueous and Hydroalcoholic Systems, Sep. 16, 2009.
Newman, Diane et al., "Review of Intermittent Catheterization and Current Best Practices," Urol Nurs. 2011:31(1).
PCT/US13/71046 filed Nov. 20, 2013 International Search Report and Written Opinion dated Feb. 21, 2014.
PCT/US13/71060 filed Nov. 20, 2013 International Search Report and Written Opinion dated Jan. 30, 2014.
U.S. Appl. No. 11/104,388, filed Apr. 12, 2005 Notice of Allowance dated Mar. 21, 2014.
U.S. Appl. No. 13/047,175, filed Mar. 14, 2011 Final Office Action dated Mar. 17, 2014.
U.S. Appl. No. 13/682,420, filed Nov. 20, 2012 Final Office Action dated Jul. 15, 2014.
U.S. Appl. No. 13/682,420, filed Nov. 20, 2012 Non-Final Office Action dated Apr. 2, 2014.
Vapro Product Brochure, 2009.
U.S. Appl. No. 13/047,175, filed Mar. 14, 2011 Examiner's Answer dated Nov. 4, 2014.
U.S. Appl. No. 13/705,695, filed Dec. 5, 2012 Non-Final Office Action dated Aug. 26, 2014.
EP 12159487.3 filed Mar. 14, 2012 Office Action dated Oct. 12, 2015.
EP 12159487.3 filed Mar. 14, 2012 Third Party Observations dated Sep. 8, 2015.
U.S. Appl. No. 13/682,420, filed Nov. 20, 2012 Examiner's Answer dated Apr. 8, 2015.
U.S. Appl. No. 13/705,695, filed Dec. 5, 2012 Final Office Action dated Apr. 23, 2015.
U.S. Appl. No. 14/508,450, filed Oct. 7, 2014 Non-Final Office Action dated Jun. 29, 2015.
EP 13856790.4 filed Apr. 28, 2015 Extended European Search Report dated Jul. 1, 2016.
EP 13857538.6 filed Apr. 29, 2015 Extended European Search Report dated Jun. 17, 2016.
MX/a/2014/005144 filed Apr. 28, 2014 Office Action dated Jul. 14, 2016.
CN 201380060741.2 filed May 20, 2015 First Office Action dated May 3, 2016.
CN201280065776.0 filed Jul. 1, 2014, First Office Action dated Jun. 4, 2015.
CN201280065776.0 filed Jul. 1, 2014, Second Office Action dated Jan. 20, 2016.
PCT/US2012/068248 filed Dec. 6, 2012 International Preliminary Report on Patentability dated Jun. 10, 2014.
CN 201380060729.1 filed May 20, 2015 Office Action dated Jul. 26, 2017.
CN 201380060741.2 filed May 20, 2015 Office Action dated Aug. 9, 2017.
JP 2015-543140 filed May 14, 2015 Office Action dated Jul. 6, 2017.

(56) References Cited

OTHER PUBLICATIONS

U.S. Appl. No. 13/682,420, filed Nov. 20, 2012 Decision on Appeal dated Jun. 16, 2017.
CN 201380060729.1 filed May 20, 2015 Office Action dated Nov. 4, 2016.
CN 201380060741.2 filed May 20, 2015 Office Action dated Dec. 19, 2016.
EP 12159487.3 filed Mar. 14, 2012 Third Party Observations dated Dec. 2, 2016.
CN 201380060729.1 filed May 20, 2015 Office Action dated Feb. 6, 2018.
JP 2015-543140 filed May 14, 2015 Notice of Allowance dated Feb. 22, 2018.
MX/a/2015/006059 filed May 13, 2015 Office Action dated Mar. 14, 2018.

\* cited by examiner

SHEATH FOR SECURING URINARY CATHETER

FIELD

The present invention relates to a device that secures a straight or Foley catheter in the urinary tract of a male subject. The device includes a portion that can be coupled to the subject's penis and a portion that can be coupled to the straight or Foley catheter. The present invention also relates to methods of making and using this device and to assemblies including the device and a straight or Foley catheter.

BACKGROUND

Movement of an urinary catheter when it resides in a subject's urethra or bladder can be uncomfortable for the subject. There remains a need for devices that can reduce or eliminate movement of a catheter after it has been inserted into a subject's urethra.

SUMMARY

The present invention includes a catheter retention sheath. The catheter retention sheath can include a sheath configured to fit over a penis. The sheath can include a catheter retainer, which can be configured to couple to a shaft of a urinary catheter. The catheter retainer can define an aperture. A first portion of the aperture can be configured to allow axial movement of the shaft of the urinary catheter through the aperture. A second portion of the aperture can be configured to retain the shaft of the urinary catheter.

The present invention includes a method of catheterizing a subject. This method can include providing a catheter retention sheath. This catheter retention sheath can include a catheter retainer configured to couple to a shaft of a urinary catheter. The catheter retainer can define an aperture. A first portion of the aperture can be configured to allow axial movement of the shaft of the urinary catheter through the aperture. A second portion of the aperture can be configured to retain the shaft of the urinary catheter. This method also includes inserting a shaft of a urinary catheter into the first portion of the aperture, inserting a portion of the shaft of the urinary catheter into a subject's urethra, and urging the shaft of the urinary catheter from the first portion of the aperture into the second portion of the aperture.

The present invention includes a method of making a catheter retention sheath. This method includes applying silicone rubber to a portion of a mandrel and forming an aperture in the silicone rubber. A first portion of the aperture can be configured to allow axial movement of the shaft of the urinary catheter through the aperture. A second portion of the aperture can be configured to retain the shaft of the urinary catheter. This method also includes curing the silicone rubber to form the catheter retention sheath defining the aperture.

In an embodiment, the present invention includes a catheter system. The catheter system includes a urinary catheter having a shaft and the present catheter retention sheath.

DETAILED DESCRIPTION

Figure 1:
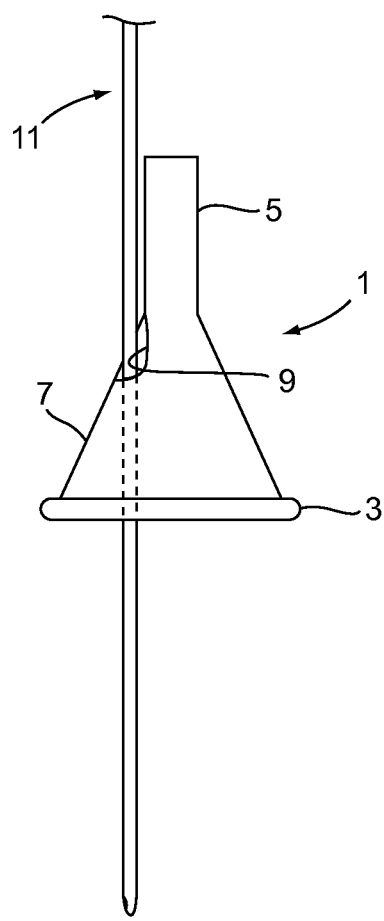
FIG. 1 schematically represents an embodiment of a catheter system according to the present invention and including an embodiment of the present catheter retainer and a urinary catheter including a shaft.

The present invention relates to a device that secures a urinary catheter (e.g., a straight or Foley catheter) in the urinary tract of a male subject. The device includes a portion that can be coupled to the subject's penis and a portion that can be coupled to the straight or Foley catheter. The portion that can be coupled to the subject's penis can be in the form of a sheath or condom configured to fit a penis, e.g., a normal, flaccid penis. The device including the sheath or condom portion and the portion that couples to the urinary catheter can be referred to as a catheter retention sheath.

The portion of the catheter retention sheath that couples to the urinary catheter can define an aperture with two portions. A first portion of the aperture is configured so that the urinary catheter can move freely (at least in the direction of the axis of its shaft) through this first portion. This first portion of the aperture can be larger than the outside diameter of a shaft of the urinary catheter and can allow the urinary catheter into and through the sheath or condom portion. A second portion of the aperture can be configured to restrict motion of the urinary catheter. For example, this second portion of the aperture can, in a relaxed state, be approximately the same size as or smaller than the outside diameter of the shaft of the urinary catheter. The urinary catheter can be lodged in this second portion of the aperture and its motion restricted with respect to the sheath and the subject (at least in the direction of the axis of its shaft).

The portion of the catheter retention sheath that couples to the urinary catheter can include a neck portion that defines part or all of the second portion of the aperture. This neck portion can include, for example, a tube with a slit along it that is coupled to the sheath portion.

The present invention includes a catheter retention sheath. The catheter retention sheath can include a sheath configured to fit over a penis. The sheath can include a catheter retainer, which can be configured to couple to a shaft of a urinary catheter. The catheter retainer can define an aperture. A first portion of the aperture can be configured to allow axial movement of the shaft of the urinary catheter through the aperture. A second portion of the aperture can be configured to retain the shaft of the urinary catheter.

In an embodiment, the first portion of the aperture is larger than the outside diameter of a shaft of the urinary catheter. For example, the first portion of the aperture can be configured to allow the urinary catheter into and through the sheath or condom portion of the catheter retention sheath.

In an embodiment, the second portion of the aperture is configured to immobilize the urinary catheter in the sheath. In an embodiment, after the urinary catheter is inserted in the subject, the second portion of the aperture is configured to restrict motion of the urinary catheter with respect to the subject's penis and bladder. For example, the second portion of the aperture is, in a relaxed state, approximately the same size as or smaller than the outside diameter of the shaft of the urinary catheter. In an embodiment, the catheter retainer defines a slit that couples the first portion of the aperture to the second portion of the aperture.

In an embodiment, the present catheter retention sheath includes a neck portion that defines part or all of the second portion of the aperture. In an embodiment, the neck portion includes a tube coupled to the sheath, the tube defining an axial slit. In an embodiment, the catheter retainer includes an integral conical portion of thicker material that defines part or all of the second portion of the aperture.

The present catheter retention sheath can be employed with any of a variety of urinary catheters. Suitable urinary catheters include a straight catheter and a Foley catheter.

In an embodiment, the sheath includes an inner surface and an outer surface, the inner surface including an adhesive configured to adhere to the penis. For example, the sheath can include a tubular sleeve member of resilient material rolled outwardly upon itself, the sleeve member having an outer surface and an inner surface. The outer surface of the sleeve member can contact a layer of adhesive and the layer of adhesive can contact the inner surface of the sleeve member. In an embodiment, the adhesive includes or is a hydrocolloid composition. In an embodiment, the adhesive composition is between the inner and outer surfaces of one or more consecutive rolls so that the adhesive is covered by the inner surface when the sheath is in rolled up condition.

In an embodiment, the present catheter retention sheath includes an adhesive band made of resilient material and configured to retain the sheath on the penis.

In an embodiment, the catheter retention sheath is made of a composition including silicone. For example the catheter retention sheath can be made of silicone rubber. In an embodiment, the catheter retention sheath consists of silicone rubber.

In an embodiment, the present invention includes a catheter system. The catheter system includes a urinary catheter having a shaft and the present catheter retention sheath.

Illustrated Embodiments

FIG. 1 schematically illustrates an embodiment of a catheter retention sheath according to the present invention and a straight urinary catheter. Catheter retainer 1 includes a sleeve 3, a tube 5, and a transition section 7 between the sleeve 3 and tube 5. Sleeve 3 is illustrated in its rolled configuration. Transition section 7 defines catheter access opening 9, which is configured to allow movement of a straight urinary catheter 11. In FIG. 1, straight urinary catheter 11 is shown protruding through catheter access opening 9 in a configuration suitable, for example, for insertion into a subject. Tube 5 defines catheter retention opening (shown in FIGS. 2 and 3), which is configured to reduce movement of or to immobilize straight urinary catheter 11.

Figure 2:
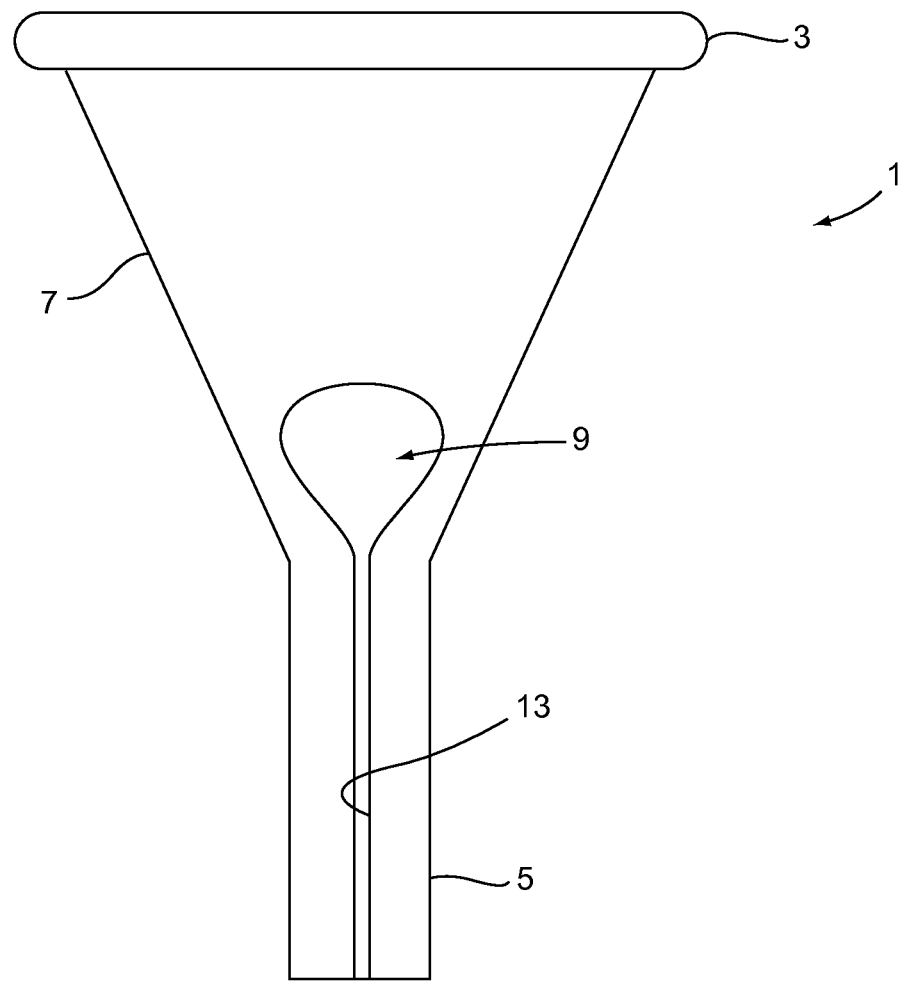
FIG. 2 schematically represents an embodiment of the present catheter retainer.
Figure 3:
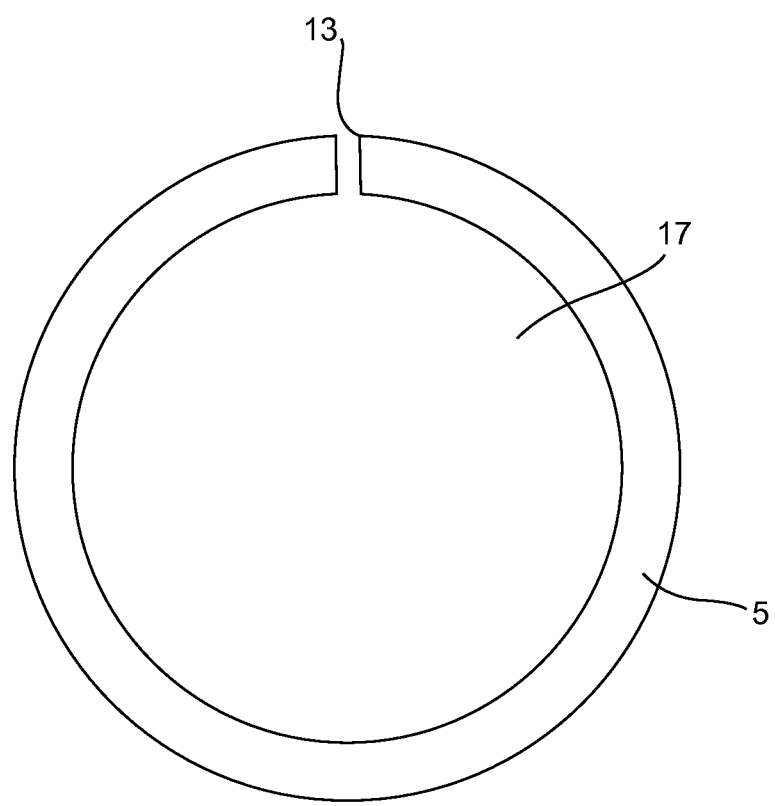
FIG. 3 schematically represents an embodiment of the present tube showing an embodiment of a lumen and of a slit.

FIG. 2 schematically illustrates another view of the catheter retainer 1 of FIG. 1 and showing tube 5, catheter access opening 9, and slit 13, which is defined by tube 5. Slit 13 and a lumen (shown in FIG. 3) of tube 5 form catheter retention opening 15. FIG. 3 schematically illustrates tube 5 showing lumen 17 and slit 13, which form catheter retention opening 15.

Figure 4:
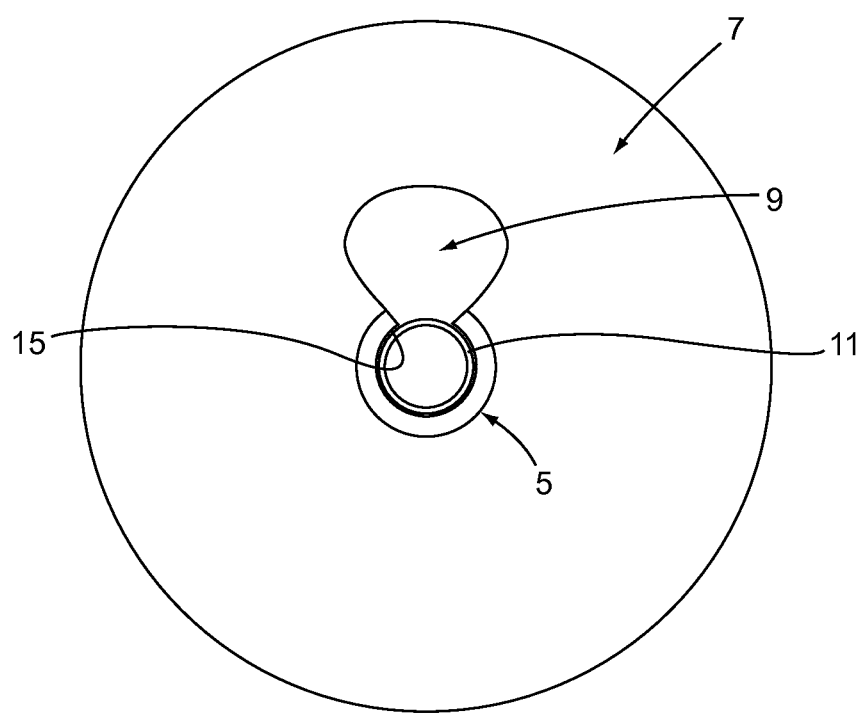
FIG. 4 schematically represents an embodiment of a catheter system according to the present invention and including an embodiment of the present catheter retainer and a urinary catheter including a shaft. The urinary catheter is shown in an embodiment of the catheter retention opening.

FIG. 4 schematically illustrates an embodiment of catheter retainer 1 with a straight urinary catheter in catheter retention opening 15 defined by tube 5. Straight urinary catheter 11 can be urged into lumen 17 from catheter access opening 9. In an embodiment, the straight urinary catheter 11 has been inserted into the subject's urethra before it is positioned in the catheter retention opening. Sleeve 3 is not shown in FIG. 4, but could be in its rolled configuration when the straight urinary catheter 11 is being inserted into the subject's urethra and then unrolled onto the subject's penis after insertion.

Figure 5:
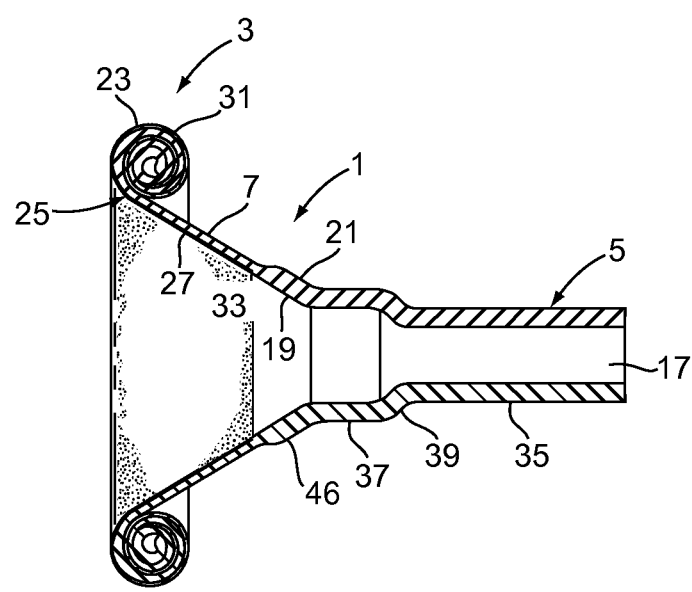
FIG. 5 schematically represents a cross-sectional view of the present catheter retention sheath including a rolled-up sheath portion.

FIG. 5 schematically illustrates features of an embodiment of catheter retainer 1 without showing straight urinary catheter 11, access opening 9, or slit 13. In this embodiment, catheter retainer 1 has a unitary construction which includes a sleeve 3, a tube 5, and a transition section 7 between the sleeve 3 and tube 5. Catheter retainer 1 can be made of silicone rubber. Catheter retainer 1 has an inner surface 19 and an outer surface 21. Following manufacture and during pre-use storage, catheter retainer 1 can be in a pre-use configuration as shown in FIG. 1, wherein a first portion 23 of sleeve 3 is rolled up on itself so that except as indicated hereinafter inner surface 19 is rolled up against and comes into contact with outer surface 21. Interposed between most of inner surface 19 and outer surface 21 of sleeve 3 can be an adhesive layer 25. Adhesive layer 25 adheres to inner surface 19 and does not adhere to outer surface 21 when sleeve 3 is unrolled. The reason for such phenomenon is discussed in more detail hereinafter. Adhesive layer 25 can also include a second portion 27 formed on a significant portion of transition section 7. First portion 29 and second portion 27 of adhesive layer 25 can be contiguous as transition section 7 changes form to sleeve 3.

Sleeve 3 can be formed as a cylinder having a diameter appropriate for a limp penis. Sleeve 3 can have a length of about 1 to about 5 inches. The length of sleeve 3 can be selected to be long enough to provide sufficient fastening adhesion between first portion 29 of the adhesive layer 25 on the inside surface of the sleeve 3 and the penile shaft, but not so long so that the sleeve 3 cannot be completely unrolled when a recessed penis is pulled outwardly to expose the total length of penile shaft with respect to pelvic skin. First portion 29 can include all of the inner surface of sleeve 3 except an adhesive-free band 31 on the inner surface of sleeve 3 adjacent its open end. Band 31 can provide a loose end for a practitioner or user of the device to grasp and begin to roll sleeve 3 back on itself or otherwise to remove an installed catheter retainer 1.

Transition section 7 provides a reduction in diameter from sleeve 3 to tube 5. Second portion 27 to which adhesive can be applied contiguously with the hydrocolloid on first portion 29 includes most of the cone portion of transition section 7. In an embodiment, second portion 27 can provide an advantageously large adhesive surface within transition section 7 to contact and adhere to the glans penis. In an embodiment, an apex portion 33, which connects with and opens to tube 5, is free of adhesive. Sleeve 3 can be rolled in the pre-use configuration. Hence, second portion 27 on the inside surface 19 of transition section 7 may be exposed (although the entire catheter retainer 1 can be appropriately protected in a package). Sleeve 3 and transition section 7 can have a thickness which allows them to be conformed to the shape of the penis as the adhesive adheres to the penis. Tube 5 has a greater thickness so as to retain its shape and provide for suitable retention of straight urinary catheter 11.

Tube 5 can be configured to provide a structure that retains its shape (e.g., doesn't collapse) when formed in a smaller diameter section 35 and a larger diameter section 37. The device can include an optional short transitional neck 39 extends between sections 35 and 37. In an embodiment, a narrow portion 46 of the cone-shape of transition section 7 can extend between larger diameter section 37 and the rest of transition section 7 so as to provide a short portion 46 of greater thickness leading to the larger portion of transition section 7 having a thinner thickness.

Although adhesive layer 25 adheres to the inner surface 19, the adhesive layer 25 does not adhere to the outer surface 21 when sleeve 3 is unrolled. Adhesive layer 25 can be simply adhered to inner surface 19 or alternatively bonded to the inner surface 19 by a catalyzed process, for example, a vulcanizing process, in which constituents within the adhesive composition are cross-linked to constituents within the silicone rubber which is formed from an unvulcanizing silicone rubber solution overcoat layer during the vulcanizing process. Once the adhesive layer 25 is adhered or bonded to the inner surface 19 and the outer surface is formed (e.g., according to a process described hereinafter), adhesive no longer irreversibly adheres to outer surface 21. Although the adhesive will releasably adhere to outer surface 21, a moderate force separates the surfaces resulting in the adhesive remaining adhered to the inner surface 19. Contact between adhesive layer 25 and outer surface 21 is referred to as "releasable contact" or "releasable adherence." As indicated, this type of contact or adherence is characterized in that it permits a relatively easy separation of the hydrocolloid from the contacting surface.

Figure 6:
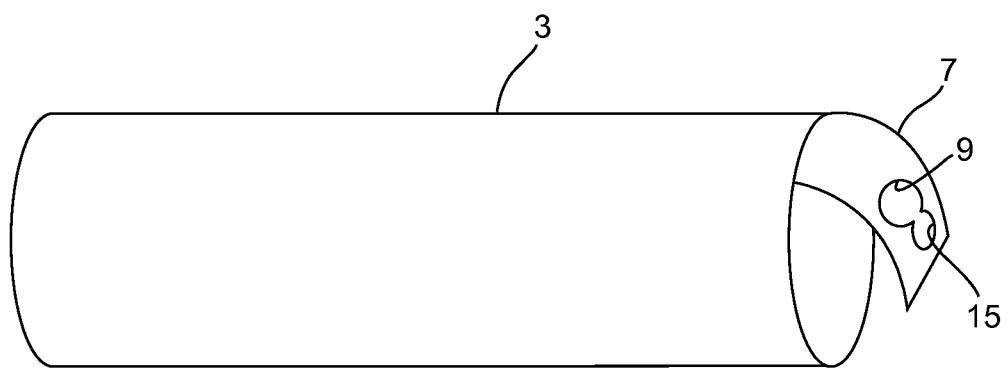
FIG. 6 schematically represents an embodiment of the present catheter retainer including a tab-shaped transition section that defines the openings.

FIG. 6 schematically illustrates an embodiment of the present catheter retainer 1 in which a tab-shaped transition section 7 defines catheter access opening 9 and catheter retention opening 15.

Sheath

The catheter retainer can have of any of a variety of configurations with a tubular sleeve or a sheath that fits over a penis. The tubular sleeve or the sheath can be made of a resilient material (e.g., silicone rubber) and can have an inner surface and an outer surface. In an embodiment, the present catheter retainer includes a sheath sized for fitting about a normal, flaccid penis.

The sheath can include a flexibly cylindrical member rolled outwardly upon itself forming consecutively larger rolls. This cylindrical member can have adhesive composition between consecutive rolls. The outer surface of the cylindrical member can release the adhesive composition when the member is unrolled and inner surface of the cylindrical member retains the adhesive when the member is unrolled. In this fashion, the sheath may be stored with the adhesive composition protected between consecutive rolls of the member and used by unrolling the member onto a penis allowing the adhesive to release from the outer surface and allowing the adhesive to adhere to the inner surface and the penis.

Adhesive

The adhesive composition can be on a portion of the inner surface. In a package and before use, the tubular sleeve or the sheath can be rolled up upon itself. In the rolled up configuration, the tubular sleeve or sheath can isolate the adhesive composition from the surroundings. For example, the adhesive composition can be between layers of the rolled sleeve or sheath. In the rolled configuration, the outer surface of the sleeve or sheath can contact the layer of adhesive composition and the layer of adhesive composition can contact the inner surface of the sleeve or sheath. For example, the adhesive composition can be between the inner and outer surfaces of one or more consecutive rolls so that the adhesive is covered by the inner surface when the sheath is rolled up.

In an embodiment, the adhesive composition is in the form of a layer that is directly and non-releasably bonded to a portion of the inner surface. The adhesive composition can releasably contact one or more portions of the outer surface. The inner surface of the silicone rubber sheath can be rolled up upon the outer surface. The layer of adhesive composition on the portion of the inner surface comes into releasable contact with one or more portions of the outer surface. The adhesive composition on the outer surface can then release from the outer surface with which it has come into contact, while remaining bonded to the inner surface, when the silicone rubber sheath is forcibly unrolled.

The adhesive can be or can include a hydrocolloid composition or adhesive. The hydrocolloid can have (strong) adhesive properties and compatibility with both skin and catheter materials. The hydrocolloid composition can include an acrylic pressure sensitive adhesive, a polyacrylic acid polymer, and, optionally, a neutralizer. The polyacrylic acid polymer can be a cross-linked polyacrylic acid polymer. Such a crosslinked polymer can provide efficient rheology modification and enhanced self-wetting. Suitable polyacrylic acid polymers include that sold under the trade name CARBOPOL ULTREZ 10 NF® by Lubrizol, Cleveland, Ohio. Suitable neutralizers include amines, such as an aminomethyl propanol.

Suitable amino methyl propanols include that sold under the trade name AMP-95® by Angus, a subsidiary of Dow Chemical. The commercial product includes 93-97 wt-% 2-amino-2-methyl-1-propanol and about 5% water. In certain embodiments, the amounts of neutralizer listed in the present application can be multiplied by, for example, about 0.93, about 0.97, or about 0.93 to about 0.97 to account for the level of active in the commercial product. In certain embodiments, the amount of neutralizer listed in the present application refers to a neutralizer stock solution that includes about 93-97 wt-% 2-amino-2-methyl-1-propanol.

For making the catheter retainer, the hydrocolloid prep composition can include about 90 to about 99.99 wt-% of acrylic pressure sensitive adhesive and solvent (about 35 to about 45 wt-% solids (e.g., the adhesive composition) the remainder being solvent); about 0.01 to about 10 wt-% (e.g., about 0.5 wt-%) polyacrylic acid polymer; and, optionally, about 0.01 to about 5 wt-% (e.g., about 0.5 wt-%) neutralizer. In an embodiment, the hydrocolloid prep composition can include about 90 to about 99.99 wt-% of acrylic pressure sensitive adhesive and solvent (about 35 to about 45 wt-% solids (e.g., the adhesive composition) the remainder being solvent); and about 0.01 to about 10 wt-% of polyacrylic acid polymer and neutralizer; the neutralizer and polyacrylic acid polymer being in a ratio of about 0.9 to about 1 (e.g., 0.9:1). The amount of neutralizer can be just sufficient to neutralize the polyacrylic acid polymer without adding additional basicity to a mixture of the polyacrylic acid and the neutralizer. In an embodiment, the neutralizer and polyacrylic acid polymer are in a ratio of 0.7-0.99:0.95-1.2 (e.g., 0.9:1). Once dried or cured on the catheter or mandrel, the hydrocolloid adhesive composition can include about 55 to about 99.98 wt-% of acrylic pressure sensitive adhesive; about 0.02 to about 30 wt-% polyacrylic acid polymer; and, optionally, about 0.02 to about 15 wt-% neutralizer.

For making the catheter retainer, the hydrocolloid prep composition can include about 90 to about 99.99 wt-% of acrylic pressure sensitive adhesive and solvent (about 35 to about 45 wt-% solids (e.g., the adhesive composition) the remainder being solvent); about 0.01 to about 10 wt-% (e.g., about 0.5 wt-%) polyacrylic acid polymer; and, optionally, about 0.01 to about 5 wt-% (e.g., about 0.5 wt-%) neutralizer. In an embodiment, the hydrocolloid prep composition can include about 90 to about 99.99 wt-% of acrylic pressure sensitive adhesive and solvent (about 35 to about 45 wt-% solids (e.g., the adhesive composition) the remainder being solvent); about 0.01 to about 10 wt-% (e.g., about 0.5 wt-%) polyacrylic acid polymer; and about 0.01 to about 5 wt-% (e.g., about 0.5 wt-%) neutralizer. In an embodiment, the hydrocolloid prep composition can include about 96 to about 99.6 wt-% of acrylic pressure sensitive adhesive and solvent (about 35 to about 45 wt-% solids (e.g., the adhesive composition) the remainder being solvent); about 0.2 to about 2 wt-% polyacrylic acid polymer; and about 0.2 to about 2 wt-% neutralizer. In an embodiment, the hydrocolloid prep composition can include about 98 to about 99.4 wt-% of acrylic pressure sensitive adhesive and solvent (about 35 to about 45 wt-% solids (e.g., the adhesive composition) the remainder being solvent); about 0.3 to about 1 wt-% polyacrylic acid polymer; and about 0.3 to about 1 wt-% neutralizer. In an embodiment, the hydrocolloid prep composition can include about 99 wt-% of acrylic pressure sensitive adhesive and solvent (about 35 to about 45 wt-% solids (e.g., the adhesive composition) the remainder being solvent); about 0.5 wt-% polyacrylic acid polymer; and about 0.5 wt-% neutralizer.

In an embodiment, the hydrocolloid prep composition can include about 90 to about 99.99 wt-% of acrylic pressure sensitive adhesive and solvent (about 35 to about 45 wt-% solids (e.g., the adhesive composition) the remainder being solvent). In an embodiment, the hydrocolloid prep composition can include about 96 to about 99.6 wt-% of acrylic pressure sensitive adhesive and solvent (about 35 to about 45 wt-% solids (e.g., the adhesive composition) the remainder being solvent). In an embodiment, the hydrocolloid prep composition can include about 98 to about 99.4 wt-% of acrylic pressure sensitive adhesive and solvent (about 35 to about 45 wt-% solids (e.g., the adhesive composition) the remainder being solvent). In an embodiment, the hydrocolloid prep composition can include about 99 wt-% of acrylic pressure sensitive adhesive and solvent (about 35 to about 45 wt-% solids (e.g., the adhesive composition) the remainder being solvent).

In an embodiment, the hydrocolloid prep composition can include about 0.01 to about 10 wt-% (e.g., about 0.5 wt-%) polyacrylic acid polymer. In an embodiment, the hydrocolloid prep composition can include about 0.2 to about 2 wt-% polyacrylic acid polymer. In an embodiment, the hydrocolloid prep composition can include about 0.3 to about 1 wt-% polyacrylic acid polymer. In an embodiment, the hydrocolloid prep composition can include about 0.5 wt-% polyacrylic acid polymer.

In an embodiment, the hydrocolloid prep composition includes no added neutralizer. In an embodiment, the hydrocolloid prep composition includes no neutralizer. In an embodiment, the hydrocolloid prep composition can include about 0.01 to about 5 wt-% (e.g., about 0.5 wt-%) neutralizer. In an embodiment, the hydrocolloid prep composition can include about 0.2 to about 2 wt-% neutralizer. In an embodiment, the hydrocolloid prep composition can include about 0.3 to about 1 wt-% neutralizer. In an embodiment, the hydrocolloid prep composition can include about 0.5 wt-% neutralizer.

Once dried or cured on the catheter or mandrel, the hydrocolloid adhesive composition can include about 55 to about 99.98 wt-% of acrylic pressure sensitive adhesive; about 0.02 to about 30 wt-% polyacrylic acid polymer; and, optionally, about 0.02 to about 15 wt-% neutralizer. In an embodiment, the hydrocolloid adhesive composition can include about 55 to about 99.96 wt-% of acrylic pressure sensitive adhesive; about 0.02 to about 30 wt-% polyacrylic acid polymer; and about 0.02 to about 15 wt-% neutralizer. In an embodiment, the hydrocolloid composition can include about 90 to about 99.4 wt-% of acrylic pressure sensitive adhesive; about 0.3 to about 5 wt-% polyacrylic acid polymer; and about 0.3 to about 5 wt-% neutralizer. In an embodiment, the hydrocolloid composition can include about 94 to about 99 wt-% acrylic pressure sensitive adhesive; about 0.5 to about 3 wt-% polyacrylic acid polymer; and about 0.5 to about 3 wt-% neutralizer. In an embodiment, the hydrocolloid composition can include about 97 to about 98 wt-% of acrylic pressure sensitive adhesive; about 1 to about 1.5 wt-% polyacrylic acid polymer; and about 1 to about 1.5 wt-% neutralizer. In an embodiment, the hydrocolloid composition can include about 97 wt-% of acrylic pressure sensitive adhesive; about 1.5 wt-% polyacrylic acid polymer; and about 1.5 wt-% neutralizer. In an embodiment, the hydrocolloid composition can include about 98 wt-% of acrylic pressure sensitive adhesive; about 1 wt-% polyacrylic acid polymer; and about 1 wt-% neutralizer.

Once dried or cured on the catheter or mandrel, the hydrocolloid adhesive composition can include about 55 to about 99.98 wt-% of acrylic pressure sensitive adhesive. In an embodiment, the hydrocolloid adhesive composition can include about 55 to about 99.96 wt-% of acrylic pressure sensitive adhesive. In an embodiment, the hydrocolloid composition can include about 90 to about 99.4 wt-% of acrylic pressure sensitive adhesive. In an embodiment, the hydrocolloid composition can include about 94 to about 99 wt-% acrylic pressure sensitive adhesive. In an embodiment, the hydrocolloid composition can include about 97 to about 98 wt-% of acrylic pressure sensitive adhesive. In an embodiment, the hydrocolloid composition can include about 97 wt-% of acrylic pressure sensitive adhesive. In an embodiment, the hydrocolloid composition can include about 98 wt-% of acrylic pressure sensitive adhesive.

Once dried or cured on the catheter or mandrel, the hydrocolloid adhesive composition can include about 0.02 to about 30 wt-% polyacrylic acid polymer. In an embodiment, the hydrocolloid composition can include about 0.02 to about 30 wt-% polyacrylic acid polymer. In an embodiment, the hydrocolloid composition can include about 0.3 to about 5 wt-% polyacrylic acid polymer. In an embodiment, the hydrocolloid composition can include about 0.5 to about 3 wt-% polyacrylic acid polymer. In an embodiment, the hydrocolloid composition can include about 1 to about 1.5 wt-% polyacrylic acid polymer. In an embodiment, the hydrocolloid composition can include about 1.5 wt-% polyacrylic acid polymer. In an embodiment, the hydrocolloid composition can include about 1 wt-% polyacrylic acid polymer.

Once dried or cured on the catheter or mandrel, the hydrocolloid adhesive composition can include about 0.02 to about 15 wt-% neutralizer. In an embodiment, the hydrocolloid composition can include about 0.02 to about 15 wt-% neutralizer. In an embodiment, the hydrocolloid composition can include about 0.3 to about 5 wt-% neutralizer. In an embodiment, the hydrocolloid composition can include about 0.5 to about 3 wt-% neutralizer. In an embodiment, the hydrocolloid composition can include about 1 to about 1.5 wt-% neutralizer. In an embodiment, the hydrocolloid composition can include about 1.5 wt-% neutralizer. In an embodiment, the hydrocolloid composition can include about 1 wt-% neutralizer.

The hydrocolloid can include a bioadhesive. Examples of suitable bioadhesives include poly(isobutylene) and acrylic adhesives. The hydrocolloid can be intimately mixed with the bioadhesive to produce an integral material.

Other suitable hydrocolloids include natural gums, such as plant exudates (gum arabic, ghatti, karaya, and tragacanth); plant seed gums (guar, locust bean and acacia), seaweed extracts (agar, algin, alginate salts and carrageenin), cereal gums (starches and modified starches), fermentation or microbial gums (dextran and xanthan gum), modified celluloses (hydroxymethylcellulose, microcrystalline cellulose and carboxymethylcellulose) pectin, gelatin, casein and synthetic gums (polyvinylpyrrolidone, low methoxyl pectin, propylene glycol alginates, carboxymethyl locust bean gum and carboxymethyl guar gum) and water-swellable or hydratable hydrocolloids. The term hydrocolloid is used regardless of the state of hydration.

Hydrocolloid compositions can include a variety of components. A hydrocolloid composition can contain, for example, an adhesive base, a gelling agent, an absorptive agent, a setting agent, an anti-microbial agent, or a mixture thereof.

Suitable adhesive bases include polyisobutylenes and acrylics, both of which possess the desirable characteristics of biocompatibility and strong adhesiveness for skin and catheter materials. Other suitable adhesive bases include any of a variety of non-toxic polymers, for example, styrene, butadiene, styrene isoprene block copolymers, urethanes, silicones, styrene butadiene copolymers, methyl acrylate copolymers, acrylic acid, polyacrylates, and blends or copolymers thereof.

Suitable bases include bioadhesives for application to the epithelium that can be compatible with mucosal surfaces and exposed dermis. When a polyisobutylene (PIB) is used, a suitable type is a hot-melt, solvent-free compound with a high molecular weight ("MW"). An example of an acceptable high MW polyisobutylene is "VISTANEX® L-140" available from Exxon Corp. and having a MW in the range of from 117,000 to 135,000 daltons. The composition can include a low MW polyisobutylene, such as "VISTANEX® LMH", with a MW in the range of from 11,600 to 12,300 daltons. The composition can include a high MW acrylic adhesive, such as "HRJ-4326", with a MW in the range of 105,000 to 125,00 daltons, available from Schenectedy International, Inc., of Schenectedy N.Y. The composition can include a lower MW acrylic adhesive, such as "HRJ-10753", with a MW in the range of 81,000-91,000 daltons, also available from Schenectedy International, Inc. In an embodiment of the hydrocolloid composition, the adhesive base makes up about 20 to about 60 wt-% of the hydrocolloid composition.

The term "bioadhesive" as used herein means an adhesive that adheres to or, for example, can strongly attach to a biological surface such as skin or mucosal tissue. Suitable bioadhesives include those that can maintain adhesion in moist or wet in vivo or in vitro environments. The strength of adherence of a hydrocolloid composition to a surface can be measured by standard tests for measuring the force, e.g. in dynes per square centimeter, as disclosed in U.S. Pat. No. 4,615,697.

Suitable gel agents include biocompatible compounds which, when exposed to water or aqueous solutions, form a solid gel, gelatin or highly viscous liquid. Suitable gel agents include sodium alginate, pectin, gelatin and agar.

Suitable absorptive agents include calcium silicate, and natural or synthetic polysaccharides. Suitable polysaccharides include cellulose derivatives such as methylcellulose, cellulose acetate, carboxymethylcellulose, hydroxyethylcellulose and the like.

Certain absorptive agents possess the capability to absorb and hold water or aqueous fluids in a colloidal mass. In a typical hydrated colloidal mass, the absorbed water or aqueous fluid may weigh many times the weight of the absorptive agent. These absorptive agents include polysaccharides such as, karaya gum, tragacanth gum, pectin, guar gum, cellulose, and cellulose derivatives such as methyl cellulose, propyl cellulose, cellulose acetate and the like, along with other substances known for use in forming a solid colloid that can adhere to skin and mucosa, used alone or in combination with various adhesive bases.

Other suitable absorptive agents include those prepared optionally from partially esterified polyacrylic acid polymers, including but not limited to, polyacrylic acid polymers lightly crosslinked with a polyalkenyl polyether such as those commercially available from B. F. Goodrich, Cincinnati, Ohio, under the trademarks "CARBOPOL® 934", "CARBOPOL® 934P", "CARBOPOL® 940" and "CARBOPOL® 941."

Additional suitable absorptive agents include hydrophilic polysaccharide gums such as natural plant exudates, including karaya gum, ghatti gum, tragacanth gum, xanthan gum, jaraya gum and the like, as well as seed gums such as guar gum, locust bean gum, psillium seed gum and the like.

Setting agents suitable for the compositions include calcium salts such as calcium chloride, calcium phosphate and calcium sulphate. The corresponding magnesium salts may also be useful as setting agents.

Anti-microbial agents that can be employed in the hydrocolloid composition include an anti-fungal agent (e.g., magnesium borate) and other known topical anti-microbial agents, including bacitracin zinc, povidone iodine, benzalkonium chloride, neomycin sulfate, polymyxin B sulfate, silver sulfadiazine and mupirocin.

Hydrocolloid Containing Silicone Sheath

In an embodiment, the present invention can include a sheath including a hydrocolloid silicone composition. A hydrocolloid silicone composition can include silicone rubber, a polyacrylic acid polymer, and, optionally, a neutralizer. In such an embodiment, the hydrocolloid composition can be a component of the adhesive layer, of one or more silicone rubber layers, or of both adhesive and silicone rubber layers.

In an embodiment, the present catheter retainer can include a sleeve or sheath made of a hydrocolloid silicone composition. The present catheter retainer can include a sleeve or sheath including a layer of hydrocolloid silicone composition disposed under the adhesive. Although not limiting to the present invention, it is believed that the hydrocolloid silicone composition beneath the adhesive can increase user comfort, for example, when removing the condom catheter. For example, the hydrocolloid silicone composition beneath the adhesive can reduce maceration of tissue (e.g., skin) to which the adhesive adheres.

In an embodiment, at least a portion of the resilient material can include a hydrocolloid. Or, both the adhesive and at least a portion of the resilient material include a hydrocolloid.

In an embodiment, the tubular sleeve or the sheath can be made of a resilient material (e.g., silicone rubber, a hydrocolloid silicone composition, or layers of both) and can have an inner surface and an outer surface.

In an embodiment of the present method of making the present catheter retainer, the method can include applying a hydrocolloid silicone composition to the mandrel and over an adhesive composition; and curing the silicone rubber to form a condom catheter comprising a layer of hydrocolloid adhesive composition, a hydrocolloid silicone composition, or both; and removing the condom catheter from the mandrel.

Referring to the Figures, in an embodiment, catheter retainer 1 can be made of silicone rubber (e.g., the present hydrocolloid silicone composition). In certain embodiments, catheter retainer 1 can be made by combining two or more layers of a silicone rubber solution or of separate silicone rubber solutions. For example, one solution can be a silicone rubber solution and another solution can be a solution of a hydrocolloid silicone composition.

Methods

The present invention includes a method of catheterizing a subject. This method can include providing a catheter retention sheath. This catheter retention sheath can include a catheter retainer configured to couple to a shaft of a urinary catheter. The catheter retainer can define an aperture. A first portion of the aperture can be configured to allow axial movement of the shaft of the urinary catheter through the aperture. A second portion of the aperture can be configured to retain the shaft of the urinary catheter. This method also includes inserting a shaft of a urinary catheter into the first portion of the aperture, inserting a portion of the shaft of the urinary catheter into a subject's urethra, and urging the shaft of the urinary catheter from the first portion of the aperture into the second portion of the aperture.

The present invention includes a method of making a catheter retention sheath. This method includes applying silicone rubber to a portion of a mandrel and forming an aperture in the silicone rubber. A first portion of the aperture can be configured to allow axial movement of the shaft of the urinary catheter through the aperture. A second portion of the aperture can be configured to retain the shaft of the urinary catheter. This method also includes curing the silicone rubber to form the catheter retention sheath defining the aperture.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A catheter retention sheath, comprising:
a sheath configured to fit over a penis;
the sheath comprising a catheter retainer, the catheter retainer configured to couple to a shaft of a urinary catheter;
the catheter retainer defining an aperture, a first portion of the aperture being configured to allow axial movement of the shaft of the urinary catheter through the aperture, a second portion of the aperture being configured to retain the shaft of the urinary catheter, wherein urine flow through the shaft of the urinary catheter is unobstructed when the shaft is retained in the second portion.

2. The catheter retention sheath of claim 1, wherein the first portion of the aperture is larger than an outside diameter of the shaft of the urinary catheter.

3. The catheter retention sheath of claim 2, wherein the first portion of the aperture is configured to allow the urinary catheter into and through the sheath.

4. The catheter retention sheath of claim 1, wherein the second portion of the aperture is configured to immobilize the urinary catheter in the sheath.

5. The catheter retention sheath of claim 1, wherein, after the urinary catheter is inserted in a subject, the second portion of the aperture is configured to restrict motion of the urinary catheter with respect to the subject.

6. The catheter retention sheath of claim 1, wherein the second portion of the aperture is, in a relaxed state, approximately the same size as or smaller than an outside diameter of the shaft of the urinary catheter.

7. The catheter retention sheath of claim 1, further comprising a neck portion that defines part or all of the second portion of the aperture.

8. The catheter retention sheath of claim 7, wherein the neck portion comprises a tube coupled to the sheath, the tube defining an axial slit.

9. The catheter retention sheath of claim 1, wherein the catheter retainer comprises an integral conical portion of thick material that defines part or all of the second portion of the aperture, the thick material being thicker than material of the sheath.

10. The catheter retention sheath of claim 1, wherein the catheter retainer further defines a slit that couples the first portion of the aperture to the second portion of the aperture.

11. The catheter retention sheath of claim 1, wherein the urinary catheter comprises a straight catheter or a Foley catheter.

12. The catheter retention sheath of claim 1, wherein the sheath further comprises an inner surface and an outer surface, the inner surface comprising an adhesive configured to adhere to the penis.

13. The catheter retention sheath of claim 1, further comprising a band made of resilient material and configured to retain the sheath on the penis.

14. The catheter retention sheath of claim 1, wherein the catheter retention sheath is made of a composition comprising silicone.

15. The catheter retention sheath of claim 1, wherein the catheter retention sheath is made of silicone rubber.

16. The catheter retention sheath of claim 1, wherein the sheath comprises a tubular sleeve member of resilient material rolled outwardly upon itself, the sleeve member having an outer surface and an inner surface;
wherein the outer surface of the sleeve member contacts a layer of adhesive and the layer of adhesive contacts the inner surface of the sleeve member.

17. The catheter retention sheath of claim 16, wherein the layer of adhesive comprises a hydrocolloid composition.

18. The catheter retention sheath of claim 16, wherein the layer of adhesive composition is between inner and outer surfaces of one or more consecutive rolls so that the layer of adhesive is covered by the inner surface of the sleeve member when the sheath is in rolled up condition.

19. The catheter retention sheath of claim 1, wherein the second portion of the aperture forms a curved shape with a radius that is the same as or smaller than a radius of the shaft of the urinary catheter between a longitudinal axis of the shaft of the urinary catheter and an outer surface of the urinary catheter.

20. A catheter retention sheath, comprising:
a sheath configured to fit over a penis;
the sheath comprising a catheter retainer, the catheter retainer configured to couple to a shaft of a urinary catheter;
the catheter retainer defining an aperture, a first portion of the aperture being configured to allow axial movement of the shaft of the urinary catheter through the aperture, a second portion of the aperture being configured to retain the shaft of the urinary catheter, wherein the second portion of the aperture is configured to immobilize the urinary catheter in the sheath.

21. A catheter retention sheath, comprising:
a sheath configured to fit over a penis;
the sheath comprising a catheter retainer, the catheter retainer configured to couple to a shaft of a urinary catheter;
the catheter retainer defining an aperture, a first portion of the aperture being configured to allow axial movement of the shaft of the urinary catheter through the aperture, a second portion of the aperture being configured to retain the shaft of the urinary catheter, wherein the second portion of the aperture forms a curved shape with a radius that is the same as or smaller than a radius of the shaft of the urinary catheter between a longitudinal axis of the shaft of the urinary catheter and an outer surface of the urinary catheter.

* * * * *